United States Patent [19]
Kelleher

[11] Patent Number: 6,063,396
[45] Date of Patent: *May 16, 2000

[54] METHODS AND COMPOSITIONS FOR THE MODULATION OF CELL PROLIFERATION AND WOUND HEALING

[75] Inventor: Peter Joseph Kelleher, The Woodlands, Tex.

[73] Assignee: Houston Biotechnology Incorporated, The Woodlands, Tex.

[*] Notice: This patent is subject to a terminal disclaimer.

[21] Appl. No.: 08/600,381

[22] Filed: Feb. 12, 1996

Related U.S. Application Data

[63] Continuation-in-part of application No. 08/483,795, Jun. 7, 1995, Pat. No. 5,618,553, which is a continuation-in-part of application No. 08/329,366, Oct. 26, 1994, abandoned, which is a continuation of application No. PCT/US95/13715, Oct. 24, 1995.

[51] Int. Cl.$^7$ ..................................................... A61F 2/02
[52] U.S. Cl. ........................... 424/428; 424/427; 514/912
[58] Field of Search .................................. 424/427, 428; 514/912

[56] References Cited

U.S. PATENT DOCUMENTS

| | | | |
|---|---|---|---|
| 4,093,709 | 6/1978 | Choi et al. | 429/19 |
| 4,937,270 | 6/1990 | Hamilton et al. | 514/777 |
| 5,017,229 | 5/1991 | Burns et al. | 106/162 |
| 5,080,924 | 1/1992 | Kamel et al. | 427/2 |
| 5,098,443 | 3/1992 | Parel et al. | 623/4 |
| 5,246,698 | 9/1993 | Leshchiner et al. | 424/78.08 |
| 5,501,856 | 3/1996 | Ohtori et al. | 424/428 |
| 5,554,187 | 9/1996 | Rizzo, III | 623/6 |
| 5,578,079 | 11/1996 | Kamel et al. | 623/6 |
| 5,618,553 | 4/1997 | Kelleher | 424/428 |
| 5,728,751 | 3/1998 | Patnaik | 523/112 |

FOREIGN PATENT DOCUMENTS

| | | | |
|---|---|---|---|
| 0430539 | 6/1991 | European Pat. Off. | A61K 9/22 |
| 0488401 | 6/1992 | European Pat. Off. | A61K 9/00 |
| WO 95/03783 | 2/1995 | WIPO | |
| WO 95/33492 | 12/1995 | WIPO | |

OTHER PUBLICATIONS

Kay et al., *Ophthalmic Surgery*,(1986) 17: 796–801.
Kang et al., *BioMaterials*, (1993) 14: 787–792.
Lee et al., *Ophthalmology* (1987) 94: 1523–1530.
Merkli et al., *Journal of Controlled Release*, (1994) 29: 105–112.
Miron et al., *Journal of Solid–Phase Biochemistry*, (1976) 1: 225–236.
Mosbach, K., *Methods in Enzymology*, (ed. 1976): 118–135.
Pasternak et al., *Life Sciences*, (1976) 18: 977–982.
Arora et al., *European Journal of Obstetrics & Gynecology*, (1994) 55: 179–182.
Blandford et al., *Investigative Ophthalmology and Visual Science*, (1992) 33: 3430–3435.
Diamond et al., *Fertility and Sterility*, (1991) 55: 389–394.
Haney & Doty, *Fertility and Sterility*, (1993) 60: 550–558.
Hill–West et al., *Obstetrics and Gynecology*, (1994) 83: 59–64.
Pietersz, G., *Bioconjugate Chem.*, (1990) 1: 89–95.
Pouyani & Prestwich, *Bioconjugate Chem.*, (1994) 5: 339–347.

(List continued on next page.)

*Primary Examiner*—Carlos A. Azpuru
*Attorney, Agent, or Firm*—Lahive & Cockfield, LLP; Jane E. Remillard; Megan E. Williams

[57] ABSTRACT

Implants which are capable of sustained release of a cell proliferation modulating agent, together with methods for their preparation and use, are provided. The proliferation modulating agent is associated either covalently or non-covalently with the material from which the implant is prepared, generally a biologically inert polymer which is physiologically compatible. The implants are implanted in the tissue, and the drug is released such that the drug is substantially retained within the implant region. The device can be used to inhibit cellular proliferation around the implant. The device can be provided as a sterile kit, preferably in a form suitable for immediate use.

33 Claims, 2 Drawing Sheets

OTHER PUBLICATIONS

Reigel et al., *Pediatr. Neurosurg.*, (1993) 19: 250–255.

Rubsamen et al., *Archives of Ophthalmology*, (1994) 112: 407–413.

Sahin & Saglam, *Acta Obstet. Gynecol. Scand.*, (1994) 73: 70–73.

Susanna et al., *Ophthalmic Surgery*, (1994) 25: 458–462.

Wiskind et al., *Obstetrics and Gynecology*, (1993) 81: 1025–1028.

Yaacobi et al., *Journal of Surgical Research*, (1993) 55: 422–426.

Yamamoto et al., *Journal of Medical Chemistry*, (1972) 15: 872–875.

METHODS AND COMPOSITIONS FOR THE MODULATION OF CELL PROLIFERATION AND WOUND HEALING

CROSS-REFERENCE TO RELATED APPLICATIONS

This application is a continuation-in part of U.S. Ser. No. 08/483,795, filed Jun. 7, 1995, now U.S. Pat. No. 5,618,553, which is a continuation-in-part of U.S. Ser. No. 08/329,366, filed Oct. 26, 1994, now abandoned. This application is also a continuation of PCT/US95/13715, filed Oct. 24, 1995.

INTRODUCTION

1. Field of the Invention

This invention relates to methods and compositions featuring polymer implants associated with cell proliferation modulating agents. The invention provides for the modulation of cell proliferation and/or wound healing at sites immediately adjacent to the implant and for the inhibition of cell adhesion to the implant itself.

2. Background

The inappropriate proliferation of cells in an organism may lead to a variety of disease states. The particular symptoms will vary depending on the type of proliferative cell and on the location of the cell. These disease states may range from cancerous malignancies when the cell is a cancer cell, to scarring when the cell type is a normal fibroblast, or to a skin disease when the proliferating cell is an epithelial or dermal cell forming a part of the integument or skin.

Proliferation of cells in various tissues of the eye can lead to impaired vision. One such example of impaired vision results from a proliferation of lens epithelial cells which remain associated with the lens capsule following cataract surgery. Specifically, extracapsular cataract extraction for the removal of cataracts frequently is accompanied by an undesired proliferation of lens epithelial cells, resulting in posterior lens capsule opacification. Virtually all pediatric patients and approximately 50% of adult patients undergoing extracapsular cataract extraction develop an opaque secondary cataract within three to five years of surgery.

Various cytotoxic agents are reported to inhibit secondary cataract formation or posterior lens capsule opacification. For example, cytotoxic agents such as 5-fluorouracil, methotrexate, colchicine, and daunomycin have been instilled into the anterior chamber of the eye to kill residual lens epithelial cells for prevention of posterior lens capsule opacification. These drugs have been delivered, e.g., by injection or with the aid of various drug delivery techniques that provide for diffusion of the drug within the eye.

A second example of vision-threatening cellular proliferation occurs following glaucoma surgery. Glaucoma encompasses a heterogeneous group of eye diseases characterized by a classical triad of symptoms: elevated intraocular pressure (IOP), optic nerve damage and progressive visual field loss. The increase in IOP is due to a decrease in the outflow of aqueous humor, the fluid in the anterior segment of the eye that is responsible for maintaining pressure balance for the entire eye. Current medical therapy for glaucoma involves the administration of one or more ocular agents, including beta-blockers (e.g., timolol), miotics (e.g., pilocarpine), adrenergic agonists (e.g., epinephrine) and carbonic anhydrase inhibitors (e.g., acetazolamide). While most glaucoma patients initially respond to drug therapy, many become refractory over time. For those individuals, maintenance of normal IOP requires surgical intervention.

Surgical techniques for the correction of glaucoma include various types of glaucoma filtering surgery (GFS), during which a drainage channel is created for aqueous humor outflow from the anterior chamber in order to lower IOP. The most successful GFS is that which uses the creation of a filtering bleb or drainage fistula, which is an elevation of the conjunctiva at the surgical site, to decrease IOP. Numerous techniques may be employed to maintain the patency of the bleb or fistula, including the use of biocompatible plastic tubes or valves, yet scarring over of the drainage channel frequently causes blockage of the bleb or fistula and a concomitant increase in IOP. Recent clinical studies have demonstrated that introduction of agents which inhibit the wound healing process can in some instances improve the success rate of GFS. These agents typically are administered by non-specific means such as application by sponge to the drainage filter tissue during the surgical procedure or by repeated, painful injections into the conjunctiva after the operation.

Drug delivery techniques which have been reported both for prevention of secondary cataracts and for GFS rely to a greater or lesser extent upon diffusion of the administered drug to the target cell site. However, the continuous movement of the aqueous fluid through the anterior chamber of the eye can alter the effective concentration of the drug at the target cell site. Thus, these delivery techniques create undesirable side effects due to the inherent activity of the modulating agent on cells other than target cells combined with the lack of specific localization to the target site, resulting in a lower effective dose at that site. For example, the non-specific delivery of potent antiproliferative agents such as mitomycin C and 5-fluorouracil often has resulted in inadequate wound healing, leakage of the aqueous humor, hypotony or very low pressure leading to further complications. As diffusion of these agents through tissue is essentially uncontrolled, the amount of agent required for observed activity coupled with the need for repeated application may be responsible for poor healing of surgical sites, and other complications.

Uncontrolled cellular proliferation also is believed to contribute to complications associated with tissue adhesion following pelvic and abdominal surgeries. For example, postoperative abdominal adhesions are the main cause of intestinal obstruction and are frequent causes of infertility in women who have undergone abdominal surgery. Different types of biocompatible adhesion barriers have been used to prevent pelvic and abdominal tissue adhesions. To be effective, the barriers must remain intact long enough for the tissues to heal and relinquish their tendency to adhere. Examples of such barriers include derivatives of hyaluronic acid which form insoluble "hydrogels". The hyaluronic acid barriers are chemically modified by crosslinking with other polymers or low molecular weight substances to permit formation of the gels. Various drugs have been interspersed with the gels in an attempt to augment these systems. However, since the hydrogels must be modified to an extent which enables them to retain barrier properties, the amount of the drug which can be bound to the hydrogel is limited due to the amount and density of crosslinking. Release of drugs from hydrogels also depends on swelling of the gel matrix to permit diffusion of the drug from the gel matrix and typically requires the exogenous addition of chemicals to modify the polymer matrix in a manner that promotes release under physiological conditions. Exogenous addition of chemicals to the hydrogels often has negative residual effects on the healing process and alters the physiological conditions of the tissue contacted by the gel and chemicals.

It therefore would be of interest for treatment regimens which involve a surgical procedure and for which a successful outcome depends on the modification of cell proliferation, for example, inhibition of growth of lens epithelial cells in cataract surgery, fibroblasts in glaucoma filtering surgery and other cells which promote adhesion of body tissues in general, to identify methods and compositions for the delivery of agents capable of modulating cell proliferation and modulating wound healing responses in a site specific manner.

Relevant Literature

Heyrman et al. (1989), *J. Cataract Refract. Surg.*, 5:169, describes studies of drug uptake and release by polymethylmethacrylate (PMMA) and hydrogel intraocular lenses. European Patent Application 0 443 809 A2 describes an intraocular lens (IOL) coated with a hydrophilic material and including a pharmacologically active agent. U.S. Pat. No. 4,918,165 describes an antibody-cytotoxin conjugate covalently linked to an IOL. U.S. Pat. No. 4,170,043 describes an IOL coated with a biocompatible, water-soluble film. U.S. Pat. No. 4,240,163 describes an IOL coated with a medicament.

Biodegradable microcapsules for use in the eye are disclosed in Wong (U.S. Pat. No. 4,853,224). A bioerodible polymer disc containing an aqueous mixture of mitomycin is disclosed by is disclosed by Charles et al. (1991), *Ophthalmology* 98(4):503. A biodegradable ocular implant for delivery of therapeutic agents is described by U.S. Pat. No. 4,863,457, by Lee et al. (1988), *Invest. Opth. & Visual Science* 29(11):1692 and by Lee etal. (1987) *Ophthalmology* 94:1523. Kay etal. (1986) *Ophthalmic Surgery* 17(12):796 describe a collagen sponge containing 5-fluorouracil for ocular use. A wafer having a diffusion limiting membrane and containing colchicine is described by Legler et al. (1993), *J. Cataract Refract. Surg.* 19:462. See also Hartmann (1990) *Ophtalmologie*, 4:102.

U.S. Pat. No. 5,017,229 describes hyaluronic acid crosslinked with a polyanionic polysaccharide to form a water insoluble gel. A method for making crosslinked water insoluble gels of hyaluronic acid are described in U.S. Pat. No. 4,937,270. U.S. Pat. No. 5,399,351 and U.S. Pat. No. 5,246,698 describe methods for controlling adhesion formation between tissues with viscoelastic polymeric gel slurries of crosslinked hyaluronic acid. R. V. Sparer et al. 1983, Chapter 6, pages 107–119, in T. J. Roseman et al., *Controlled Release Delivery Systems*, Marcell Dekker, Inc., New York, describes sustained release of chloramphenicol convalently attached to hyaluronic acid via an ester linkage.

The following references also may be relevant to the subject invention: Xu et al. (1993), *Ophthal. Surgery*, 24(6):382–388; Tahery and Lee (1989), *J. of Ocular. Pharm.*, 5(2):155–179; Palmer (1991) *Ophthalmology*, 98:317–321; K. Mosbach (Ed.), (1976), *Methods in Enzymology*, Vol. 24 Immobilized Enzymes; S. Wong (1991) *Chemistry of Protein Conjugation and Crosslinking CRC*; G. Pietersz (1990), *G. Bioconjugate Chem.* 1:89; W. J. Power etal. (1994), *J. Cat. Refract. Surg.* 19:440; M. Weller, et al. (1988), *International Ophthalmology* 12:127; M. Bruce Shields, *Textbook of Glaucoma* (3rd ed. 1992), Ch. 34 and 36; and H. Alkock and F. W. Lampe (__ed. 1981), *Contemporary Polymer Chemistry*.

The following are general articles: Maeda et al. (1992) *Bioconj. Chem.* 3:351–362; Takakura and Hasida (1995) *Crit. Rev. Oncol. Hematol.* 18:207–231.

SUMMARY OF THE INVENTION

The present invention provides methods and compositions for modulating the proliferation of target cells. The composition comprises a polymer implant with which a cell growth modulating agent is reversibly associated under physiological conditions. The association is reversible and can be a covalent labile bond or a non-covalent reversible association. By "physiological conditions" is intended the chemical and physical conditions reflected by bodily fluids and/or tissues at a target tissue of interest. A sufficient number of reactive groups are provided by the polymer to bind an appropriate amount of agent needed to sustain release of an effective modulating amount of the agent for the desired period of time under physiological conditions. In use, the implant is contacted with a tissue comprising the target cells. Upon release from the polymer, an effective amount of the modulating agent remains substantially within a localized region of the tissue, so that the modulating agent affects primarily target cells in the localized region. The invention also provides for an intraocular device comprising a biologically inert polymer associated with a modulating agent, and methods for preparing the intraocular device. The methods and compositions find use, for example, in the prevention of secondary cataracts, in enhancing the success of glaucoma filtering surgery, in reducing post-surgical tissue adhesion and in the enhancement of biocompatibility of tissue implants by use of an antiproliferative agent as the cell proliferation-modulating agent to modulate growth of cells migrating into an implant site.

DESCRIPTION OF THE SPECIFIC EMBODIMENTS

Figure 1:
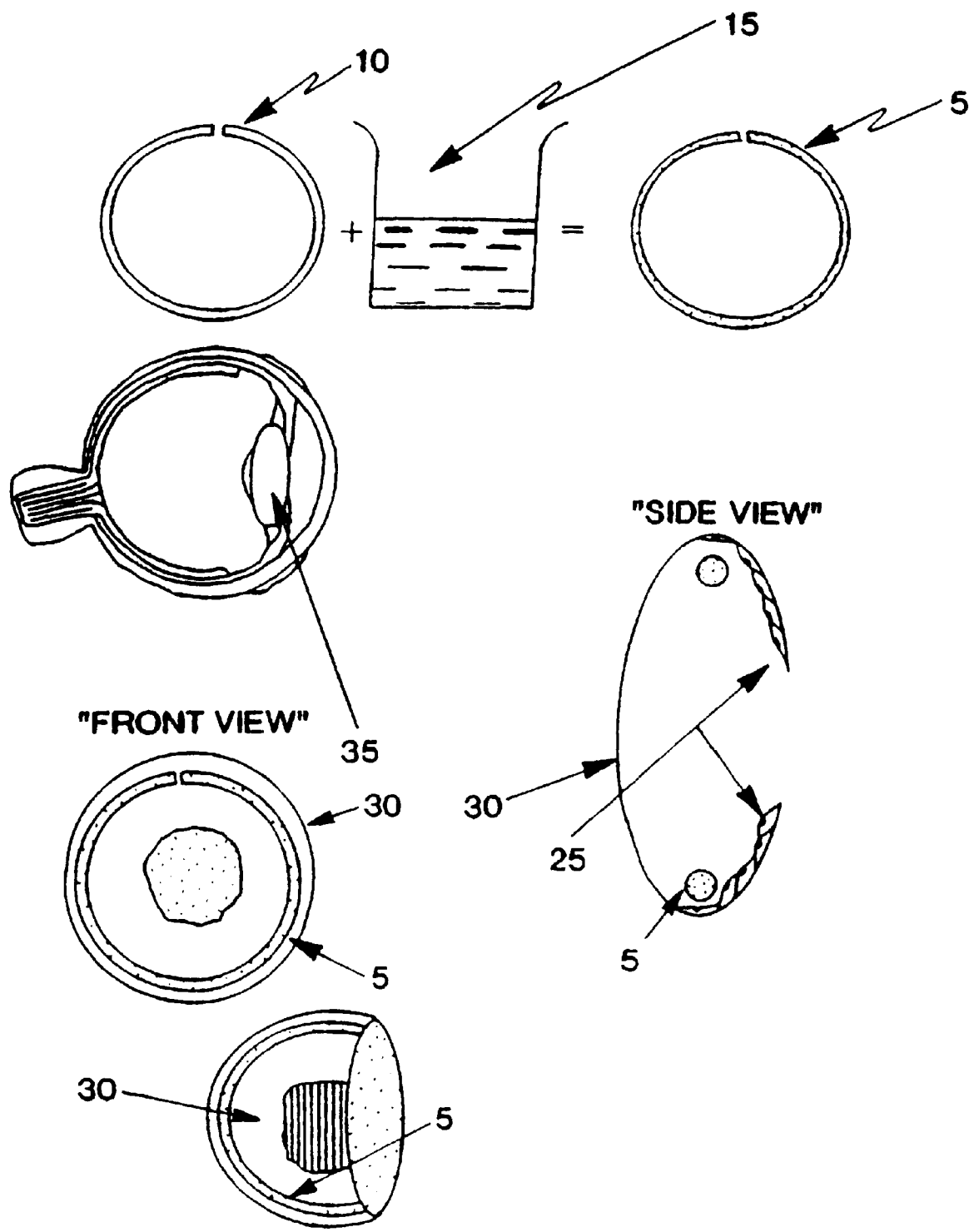
FIG. 1 shows a schematic representation of one embodiment of the invention wherein a tissue of interest is contacted with an implant composed of a polymer and a cell proliferation-modulating agent. In this embodiment, daunomycin (15) is associated with the polymer nylon which has been fabricated as a loop (10) to produce a daunomycin coated loop (5). The daunomycin coated loop (5) is inserted into the lens capsule (30) of the lens (35) following cataract surgery, thus placing the drug in close proximity to the lens epithelial cells (25) which line the inner surface of the capsule (30).
Figure 2:
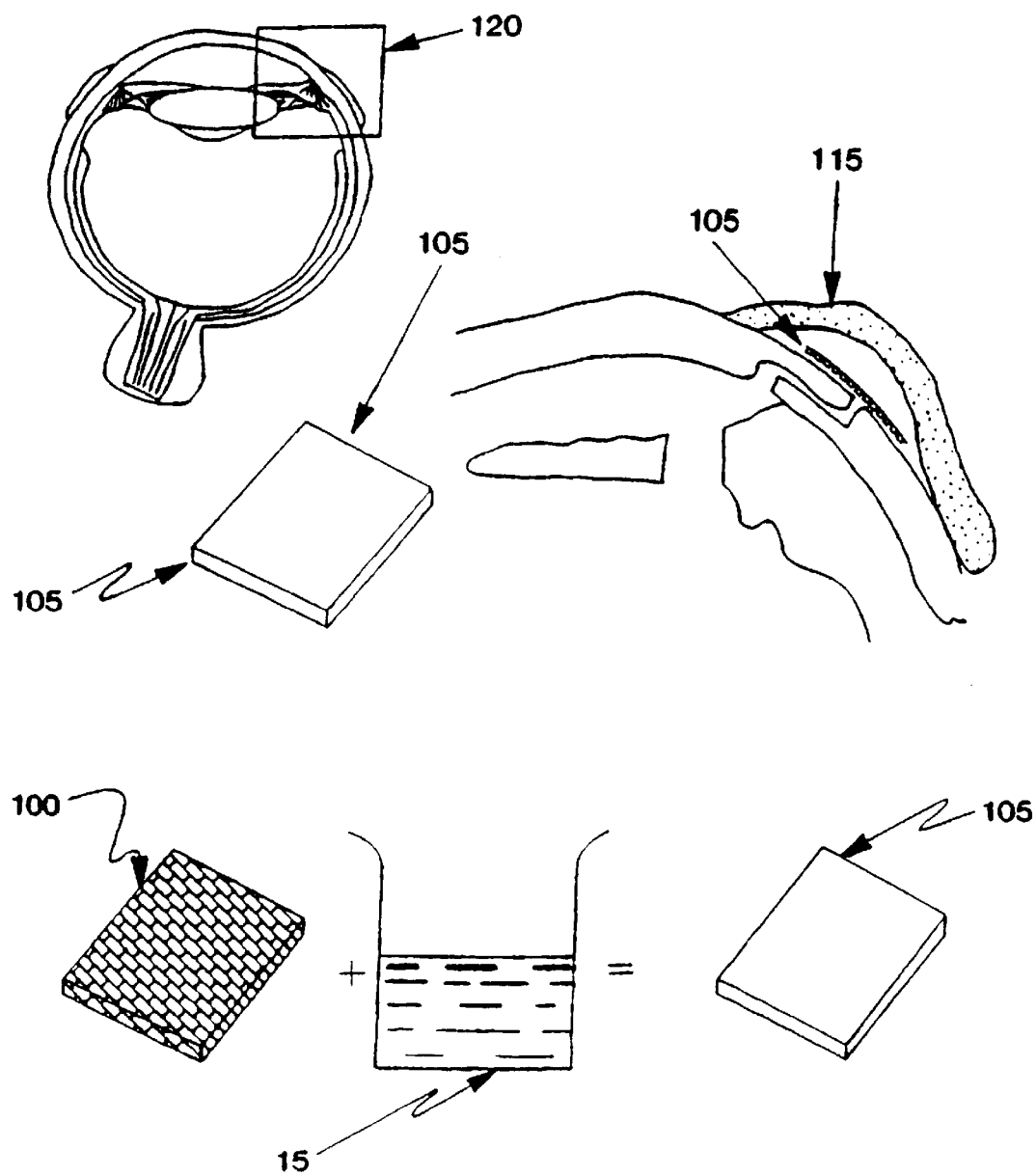
FIG. 2 shows a schematic representation of another embodiment of the invention wherein the cell proliferation-modulating agent daunomycin (15) is associated with a nylon membrane (100) to produce an implant form (105). The nylon-daunomycin implant (105) is contacted with tissue posterior to the conjunctiva in the surgically created fistula (120) following filtration surgery. Implantation at this site places the cytotoxic agent in close proximity to proliferating fibroblasts which in the absence of treatment can cause scarring over of the surgically created drainage channel (120).

The present invention provides methods and compositions for modulating cell proliferation and wound healing in a tissue of interest. In the methods, a tissue of interest is contacted with a composition which includes a cell proliferation-modulating and/or wound healing agent and a biologically inert polymer implant. The selected modulating agent is associated reversibly with the polymer implant so as to provide for localized delivery of the agent following implantation of the device into the tissue. By "polymer implant" is meant a polymer in a physical form suitable for placement within the body by surgical or other means. The polymer implants of the invention restrict the agent to the implantation site. In this way the modulating effect of the agent is concentrated at the tissue site of interest by its association with and localized release from the polymer. The amount and rate at which the agent is released also depends on its association with the polymer when the implant is formed and following implantation. In forming the implants, the polymers are modified to express reactive groups which form reversible covalent or non-covalent bonds with the modulating agent that are labile under physiological conditions. A sufficient number of reactive groups are provided on the polymer to permit loading of an effective amount of the modulating agent to achieve the desired modulating effect under physiological conditions. Loading of the modulating agent can be adjusted based on the chemistry and ratio of reactive groups to modulating agent. The ratio can be adjusted to exploit the affinity between the modulating agent and the polymer and/or the affinity of the modulating agent with the target cell and tissue of interest. In particular, the ratio of modulating agent to polymer reactive groups is adjusted to accommodate a desired equilibrium between release rate and reversible association of the modulating agent with the polymer reactive groups. Thus, the implants are designed to increase the tissue residence time of an effective growth modulating amount of the agent while minimizing side effects to other than target cells.

The actual physical shape of the polymer implant is determined by the intended use. The polymer implant can be prepared by immersing the implant into a solution of a modulating agent, whereby the agent is adsorbed to the polymer by hydrophobic/hydrophilic action, hydrogen bonding or other secondary bonding and/or by chemical linkage. In use, the polymer implant and associated agent are introduced into the tissue during or following surgery. For GFS, the implant is laid on top of the sclerostomy site (if partial thickness) in the subconjunctival space. For prevention of secondary cataracts, the implant is inserted into the lens capsule. For use in controlling tissue adhesion in surgeries in general, the implant can be formed and applied as a dry wafer, gel or membrane and the like to create an adhesion barrier.

The modulating agent is continuously released from the implant polymer at a concentration and rate sufficient to modify cell proliferation and/or wound healing of the target cells in the immediate vicinity of the implant and so have minimal or no effect on cells away from the implant site. The target cells include lens epithelial cells, in the case of secondary cataracts, and fibroblasts and leukocytes, in the case of GFS or any other application in which scarring is to be minimized.

The localized region of modulation is determined by the release characteristics of the polymer and the concentration of the modulating agent associated with the polymer, and can readily be optimized using the experimental techniques described herein. For example, for use in secondary cataract prevention, the implant resides within the remaining lens capsule, and the modulating agent is substantially localized to the equatorial region of the capsule. Localization may be further facilitated when, during normal healing, cells surround and attach to and/or encase the implant. Generally, the localized region is within 10 mm of the implant, more preferably 7 mm, most preferably 5 mm or less. The modulating activity of the implant is maximally exerted upon any cell coming into actual contact with the implant. Such contact inhibition is particularly desirable for GFS. For control of tissue adhesion in general, such as with pelvic and abdominal surgeries, the cell modulating activity of the implant is adapted to augment the tissue adhesion barrier properties of the implant. The cell modulating activity and barrier properties of the implant are facilitated by adjusting the concentration of the modulating agent originally associated with the polymer and the effective concentration of agent released by the polymer over a period of time.

The compositions and methods of the subject invention offer several advantages over currently available methods for modulating cell proliferation and/or wound healing. For example, as a result of binding of the modulating agent to a polymer implant, the modulating agent remains localized in the wound or surgical site, creating a high local concentration of the agent and minimizing or eliminating diffusion or systemic delivery to other areas. Restriction of the modulating agent to target cells located at the surgery site is accomplished by the polymer itself and the reversible association of the modulating agent with the polymer under physiological conditions. Another advantage is that the polymers of the invention are adapted to express a defined number of pendant terminal reactive groups for high capacity loading of the modulating agent and for controlling the reversible association and release of the modulating agent from the polymer under physiological conditions. Thus, overall toxicity is reduced by requiring less drug and fewer applications to achieve effective modulation of target cell proliferation. Even if there is some diffusion away to other areas, the concentration of the antiproliferative agent generally is insufficient to affect cells in those other areas. In contrast, currently available methods of applying antiproliferative agents without localization can result in complications such as poor control of proliferation and/or healing and wound leaks and negative effects on cells away from the implant site. Other advantages of the subject invention include control of the dosage of the modulating agent and prevention of unwanted effects on essential cells in the tissue of interest, since localization of the drug to the tissue site prevents migration to other areas of sensitive cells, especially normal cells, and instead sequesters the growth-modulating agent in the region of invading cells. It also is unnecessary to prepare separate formulations for each tissue of interest as the localization of the drug is accomplished by the implant. The resulting effect can, as appropriate, range from complete elimination of an undesirable cell type to inhibition of cell proliferation at the implant site, or it can be used to stimulate growth, for example, of a poorly healing wound, such as in a diabetic or a burn patient. Another advantage is that the implants of the invention are bioloigcally inert and can be provided in bioerodible and nonbioerodible forms adapted for a given use. An advantage of such implants is that the bioerodible properties can be exploited to achieve the desired level of association between the modulating agent and the polymer, the release rate of the agent from the polymer, and thus retention of a given modulating agent to the target tissue of interest while maintaining the structural and biocompatible requirements of the implants. The implants provide the advantage of improving the overall success rate of the surgery.

The compositions include a biocompatible polymer implant with which a modulating agent is associated. By "modulating agent" is meant any compound that alters the growth or development of cells, including both cell-proliferation-modulating agents and agents that affect wound healing. Examples include antimetabolites and cytotoxins which kill cells, antimitotics that further inhibit growth or proliferation of cells, growth factors which stimulate cell division, differentiation, etc., or compounds which alter the wound healing process, e.g. by selectively inhibiting or stimulating a population of cells associated with wound healing, such as fibroblasts. More than one modulating agent can be associated with the implant.

When the intended application is an inhibition of cell proliferation and/or prevention of wound healing, specific proliferation-modulating agents can include daunomycin (daunorubicin), doxorubicin, mitomycin C, 5-fluorouracil, cytosine arabinoside, colchicine, cytochalasin B, bleomycin, vincristine, vinblastine, methotrexate or the like. Suitable derivatives of these agents also can be used, such as the N-methylated derivatives of daunomycin. Also of interest are toxic agents which are derived from microorganism or plant sources. Examples include naturally occurring toxins such as ricin, abrin, diphtheria toxin, and the like. When the desired result is enhanced cell proliferation or wound healing, the proliferation-modulating agent can be a growth-promoting agent such as fibroblast growth factor, epidermal growth factor, transforming growth factor β, and platelet-derived growth factor and the like.

The polymer is biologically inert and physiologically compatible with tissues, e.g., the eye. The polymer also desirably in and of itself does not induce an inflammatory response. The polymer also preferably is capable of associating reversibly with a sufficient amount of the selected modulating agent, and of releasing that agent in a suitable manner under physiological conditions to satisfy the intended objective, e.g., inhibition of wound healing. The preferred characteristics of the polymer include capacity for interacting in a reversible manner with the modulating agent, whereby the modulating agent is released slowly into the eye or associated tissues where modulation is desired. The polymer is capable of absorbing the modulating agent either covalently or non-covalently. Examples of association include by way of electrostatic charge, hydrophobic or hydrophilic interactions, and covalently.

Various molecules which have the desired characteristics can be used to prepare the general class of polymers such as polyamides, polypeptides, polyesters, polycarbonates, polyurethanes, polyacetals, polysaccharides, and polyolefins which are used in preparing the implant. Specific examples of such polymers include, but are not limited to, silicone rubber, polyurethane rubber, polyethylene, polyvinyl chloride, poly(hydroxyethyl methacrylate), poly(methyl methacrylate), poly(ethylene terephthalate), polypropylene, polystyrene, poly(tetrafluoroethylene), polyglycolic acid, cellulose, ethylcellulose, methycellulose, dextran, carboxymethylcellulose, hyaluronic acid, hydroxypropylmethylcellulose, nylon and collagen. Additionally the implant can be a polymer and/or a salt thereof and/or a homologues, analogue, derivative, complex, fragment as well as a copolymer, composite or blend of the above.

Of particular interest are biologically inert polymer implants with which the modulating agent is associated covalently or noncovalently in an amount sufficient to provide the desired amount of modulation of cell proliferation following release of the modulating agent after insertion of the implant. One such example is a nylon polymer implant to which is adsorbed an amount of daunomycin sufficient to inhibit cell proliferation and/or wound healing. The nylon polymer to which the cell modulating agent is bound can be in the form of a membrane, or alternatively, the polymer can be in the form of a powder, which can be prepared as a wafer or other implant form by various techniques, i.e., pressure mold. Various fillers/binders and coatings can be used. Essentially the binder dissolves in aqueous solution allowing the dispersion of the particles. In a tissue this provides a more amorphous distribution than an intact implant. The biological properties of many other suitable polymers are known to the art. An example are the hyaluronans, or hyaluronic acid. The hyaluronan polymer or its derivatives to which the cell modulating agent is bound can be formed as a soluble or insoluble gel or slurry, viscoelastic gel, film, membrane and the like, or as a dry wafer or in compressed form. Hyaluronan can be modified by crosslinking among hyaluronan polymers or to other polymers or low molecular weight compounds. The source of the hyaluronan can be natural or synthetic and the hyaluronan can be of variable molecular weight. Of particular interest are the high molecular weight hyaluronans. The ability to reversibly associate a modulating agent with the polymer is readily determined by one skilled in the art for any polymer having otherwise desired biological properties using methods known to those skilled in the art. Bioerodible implants can be formulated to erode from the implant surface in contact with tissue or fluid toward the portion of the implant protected from such contact, e.g., polymers whose monomer units are linked by bonds that in general are labile under physiological conditions. Release of the modulating agent from bioerodible implants that are non-porous generally provide zero order release rates that depend on the rate of implant surface erosion under physiological conditions. Release of the modulating agent from bioerodible implants that are more porous can be used to alter the release rate kinetics by increasing surface contact area. Porosity can be controlled by a number of means known in the art including polymerization conditions, source and type of the polymer, crosslinking etc. The nonbioerodible implants are those which generally are not susceptible to erosion under physiological conditions, e.g. polymers whose monomer units are linked by bonds that generally are not labile under physiological conditions. In some instances, the bioerodible and biodegradable properties of the implants can be combined, for example, by copolymerization of nonbioerodible polymers with bioerodible polymers by methods known in the art. The bioerodible and nonbioerodible implants of the invention can be used to provide mechanical support, scaffold, or barrier properties in connection with the delivery of an effective growth modulating amount of one or more modulating agents of interest. The bioerodible and nonbioerodible implants are formulated to provide for the controlled release of the modulator agent at a rate which increases the target cell tissue residence time of an effective amount of the modulator agent of interest while minimizing contact of the modulator agent with non-target cells. Of particular interest is the control of the release rate by the ratio of the polymer to the modulator agent of interest and the nature of their reversible association. This is preferably accomplished by modification of the number and type of pendant terminal reactive groups expressed on the polymer and their reversible association with the modulator agent of interest.

It is desirable for the modulating agents to be bound reversibly to the polymer implant or via a labile bond so as to be only locally diffusible about the region in contact with that implant, thereby increasing the local concentration of the modulating agent, while reducing side effects to cells away from the implant site and the required frequency of administration. The rate of release of the growth-modulating agent from the polymer can be varied depending on the particular use. Generally, the rate of release is about 25 to 50% of the initial amount released in the first 24 hours, and 5–10% per 24 hour period, thereafter. The overall rate of release also depends on the polymer/agent affinity and equilibrium of association. The implants of the invention can be further formulated to include small molecule carriers which enhance uptake of the modulating agent by the target cells of interest.

The polymer implant can be prepared in a number of ways. For example, the modulating agent can be associated with the implant by immersing it in a solution of the modulating agent, whereby the agent becomes reversibly associated with the polymer. The modulating agent also may be reversibly bound to the implant by other coating techniques known to those skilled in the art, such as spraying the implant within the modulating agent or flowing the modulating agent about the implant. Two systems are of particular interest. The first system uses a cytotoxic agent (daunomycin, doxorubicin, etc.) absorbed onto the polymer, i.e., nylon. In aqueous solutions daunomycin is released from the nylon slowly. In the second system a covalent bond is formed between reactive groups present on the polymer and the modulating agent. Examples of such bonds are imine derivatives of the C13 carbonyl groups of doxorubicin and daunomycin, such as hydrazones and semicarbazones. These types of bonds have been described in Yamamoto, et al., *J. Medicinal Chem.* (1972) 15:872–875 and Morrison and Boyd (1966) *Organic Chemistry* (2d Ed.) (Allyn and Baeen, Inc., Boston, p. 640).

For covalent coupling of an anti-proliferative agent to the polymer, reactive pendant terminal sites such as —OH, —COOH, —SH, or —NH$_2$ can be present on the polymer, or can be introduced by procedures known to those skilled in the art. See, for example, Mosbach, *Methods of Enzymology* and Wong, *Chemistry of Protein Conjugation and Crosslinking*. Of particular interest are covalent bonds which are labile, i.e., they can be cleaved enzymatically or by acidic or reducing conditions. Covalent bonds formed through reactive hydrazido groups are of particular interest, e.g. hydrazide and dihydrazide groups. Numerous methods for coupling drugs to the above reactive sites are known to those skilled in the art. See, for example, Pietersz, *Bioconjugate Chemistry* (1990) 1:89. Where the polymer is nylon, for example, functional carboxyl and amino groups can be introduced by controlled hydrolysis using 3 M HCl. The carboxyl group can be activated with 1-ethyl-3-[3-dimethylaminopropyl)-carbodiimide (EDC) for reaction with adipic dihydrazide to provide hydrazide substituted nylon.

Modified nylons can also be produced as described by Morris, et al. *Biochem J.* (1975) 147:593 through an initial O-alkylation of the polymer with triethyloxonium tetrafluoroborate. The resulting imidate salt of nylon then is allowed to react under nonaqueous conditions with a bi-acid hydrazide, such as adipic acid dihydrazide, to give hydrazide substituted nylon.

Where the polymer is polymethyl methacrylate (PMMA) for example, carboxyl groups can be introduced by treatment with an oxygen plasma discharge, followed by acrylic acid to yield PMMA with available carboxyl groups. See, for example, Inn-Kyu Kang, et al. (1993). Of particular interest is the activation of the carboxyl group to form hydrazide reactive groups. This can be accomplished by a number of means, for example, reaction of the carboxyl group using EDC and reaction with adipic acid dihydrazide to provide hydrazide substituted PMMA.

Where the polymer is a polysaccharide such as carboxmethylcellulose, hydroxypropylmethylcellulose, hyaluronic acid, heparin or the like or a protein with naturally available carboxyl groups, the carboxyl groups can be derivatized directly by using EDC and adipic acid dihydradize, suberic and succinic dihydrazide or hydrazine in a similar manner to give hydrazide substituted polysaccharide or protein respectively. See, for example, Herwitz, et al. (1980) *J. Applied Biochem*, 2:25–35; Pouyani and Piestwich (1994) *Bioconjugate Chem.*, 5:339–347; Larson, et al. (1989) *Biomaterials* 10:511–516. The polysaccharide polymers also can be activated with cyanogen bromide or sodium periodate. For example, carboxymethylcellulose and hydroxypropylmethylcellulose can be activated with cyanogen bromide in formation of the hydrazide reactive group.

The biocompatibility of the implants can be increased, for example, by attachment of polyethylene gycol (PEG). Methods for preparing activated PEG are well known. See, for example, Bergstrom et al., (1992), *J. Biomed. Mat. Research* 26:779–790. Methods for preparing polymers with functional groups capable of reacting with these activated PEG molecules also are well known. Examples of improving the biocompatibility of implant materials with PEG have been published. Such a modification also allows for use of polymers which would be otherwise suitable for use in preparing an implant, but which are not biocompatible, or have poor biocompatibility. Other means of improving the biocompatibility of implants include the use of heparin (see, for example, Behar-Cohen et al. (1995), *Investigative Ophthalmology Visual Science* 36:5802 which discloses heparin coated intraocular lenses (IOLs)).

The polymer implant can be provided in a variety of forms. The polymer can be cast, molded or fabricated into any form suitable for the particular application. It can be a stand-alone device such as IOL, or the implant can be in a form that can be used in conjunction with another device. For use in the prevention of secondary cataracts, for example, the form of the implant can be a substantially circular ("O") ring or loop capable of fitting into the lens capsule in conjunction with an IOL. The O ring or loop has approximately the diameter of the lens and is placed in the eye so as to go around the inner periphery of the capsule. After the device is in place, an IOL is then inserted. Alternatively, for GFS, the implant can be in the form of a thin membrane or sponge. A thin polymeric membrane also can be used to encapsulate a polymeric or other implant, when it is desirable that scarring in the region of implant be minimized. For use as a tissue adhesion barrier in pelvic and abdominal surgical sites, the polymeric implant can be formed as a compressed or swollen membrane, viscoelastic gel, dry wafer implant and the like so that when implanted, the barrier remains intact until the tissues no longer have the tendency to adhere. The polymer implant can be provided in a form suitable for injection, such as an emulsion, suspension or solubilized form which retains its target cell tissue restrictive properties, i.e., the injected implant binds the target tissue or otherwise restricts the injected implant to the vicinity of the injection site by, for example, its precipitation, solidification, encapsulization or cellular uptake at the injection site.

The implant is fabricated as desired, sterilized by any acceptable means, for example, autoclave (steam) sterilization, irradiation, ethylene oxide gas, etc. It is then aseptically immersed into a sterile solution of cell proliferation modulating agent to allow for association. Following association, the implant is rinsed with water to remove unbound agent, dried and packaged. Alternatively, nylon powder (particles) can be sterilized as above, added to solution of daunomycin for example, rinsed with water to remove unbound drug, and dried. The nylon powder with associated daunomycin is then mixed with appropriate formulation agents (such as hydroxypropyl methyl cellulose (HPMC), sucrose, etc.) as binders and formed into tablets, wafers, etc. When placed into tissue, the binder dissolves leaving the nylon-daunomycin particles trapped in the tissue. The drug is slowly released from the particles.

The load capacity of the polymer for the modulating agent is determined in part by the surface area of the implant and in the case of covalent bonds, by the number of available reactive groups. The extent to which the polymer is crosslinked by the terminal pendant reactive groups will affect the load capacity of the polymer for the modulating agent. Where a high load capacity is desired, crosslinking of the polymer through its available reactive groups can be reduced or avoided to provide a sufficient number of reactive groups for binding the desired amount of modulating agent. Accordingly, implants with maximized surface areas, for example porous or woven implants, may be preferred for particular applications. The implant also may be formed so as to provide a physical gate to cell encroachment, e.g., a lip, ridge, or grid, that is designed to increase physical contact of the target cells with the implant. For example, in GFS the implant can be a membrane which can be implanted in the fistula. The membrane implant generally is designed to allow free passage of aqueous fluid from the filtration site, and generally is of a size to cover the scleral surgery site. An approximate diameter of 1 cm, and a thickness of 1–5 mm, is typical for a membrane implant. The membrane can be placed directly over the scleral surgery site, under the conjunctiva, and hence help support the fistula bleb created during GFS. The implant also can be cut to the shape of and be placed in the scleral bed in the case of a partial thickness surgery.

In use, the polymer implant and associated agent generally are introduced into the tissue during or following surgery. As an example, for GFS, the polymer implant is placed at the surgical site as follows. The conjunctiva is carefully dissected anteriorly to the limbus. Excessive tenons tissue overlying the sclera are excised. A limbal groove is made and extended anteriorly, into the corneal stroma. Before the anterior chamber is entered, a paracentesis is made through peripheral clear cornea away from the filtering site. Then the anterior chamber is entered through the filtering site and a small (1×3-mm) block of scleral tissue and trabecular meshwork is excised. The edges of the sclerectomy are cauterized to control hemostasis. Then a peripheral iridectomy is performed. The cylindrical polymer is inserted into the sclerostomy site before closure.

Following insertion of the implant, the cell proliferation-modulating or wound healing agent is continuously released from the implant polymer at a concentration and for a time sufficient to modify cell proliferation or wound healing in the immediate vicinity of the implant. The implant may exhibit a slow, steady-state release of the modulating agent such that the agent remains substantially within the region of the implant. Alternatively, the implant may exhibit a multi-phase release in which the polymer delivers an initial "burst" of short duration followed by sustained release of lower concentrations. Such a release profile also advantageously minimizes the amount of modulating agent delivered to non-target regions while advantageously exposing the target cells in the localized region to an initial exposure that rapidly initiates the desired modulation. The load bound to the support depends on the surface area of the support and the concentration of the cell modulating solution and the time. Using high concentrations, a higher amount of weakly associated drug may come as a burst. The amounts can be varied and the release modified by how extensively the implant is washed prior to use. The implant also advantageously retains sufficient concentrations of the desired modulating agent to effectively exert contact modulation upon any target cell physically contacting the implant, for at least several days following placement of the implant.

Thus, both concentration and the release rate of the growth-modulating agent can affect the time elapsed before the effect on target cells is achieved. Generally, the effect on cell proliferation of the cell-modulating agent associated with the implant polymer is realized within 24 to 48 hours after target cells come in contact with the cell-modulating agent, depending upon the concentration of the agent used. The effect generally may be expected to last for 3–5 days or longer, depending upon the release characteristics of the polymer and the potency of the modulating agent.

The effectiveness of the implant with associated cell modulating agent for its intended use can be determined in a variety of ways. Many types of cells can be used to test the complex, preferably cells similar to the cell type in the tissue of interest. For example, when the intended use of the implant is in human ocular tissue, it is preferable that human scleral fibroblast cells obtained from surgical specimens or fresh eye bank tissues be used. When the intended use is a veterinary one, it is preferable that the cells be from the intended recipient host species. For example, when the desired effect is inhibition of cell proliferation, particularly proliferation of cells which migrate into an ocular wound, the implant can be tested using an in vitro cell culture assay in which mammalian cells are added to culture wells containing the polymer implants. An in vivo model of the intended condition for treatment, such as glaucoma or secondary cataract development can be used. As an example of an in vitro assay for determining the ability of the conjugate to inhibit or stimulate cell proliferation in vitro. Alternatively, growth can be evaluated by functional determination such as the effect of the test agent on protein synthesis. For example, the stimulation of collagen formation can be monitored in vitro using the incorporation of 1-[2,3-$^3$H]-proline into collagenase susceptible protein. (Peterkofsky, B., et al., (1982) *Immunochemistry of the Extracellular Matrix Vol. II*, ed. Furthmayr, H. CRC Boca Raton, FL pp. 19–42.)

In one particular use of the polymer implant, the tissue(s) of interest are the sclera and conjunctiva of the eye, and the intended application of the invention is to enhance the success of glaucoma filtering surgery. In glaucoma filtering surgery, a drainage fistula or channel is surgically created to increase aqueous humor outflow as a means of lowering IOP. The intended application of the polymer implant in glaucoma filtering surgery is to control or down-regulate the healing of the surgical wound such that it heals, but in the process does not create excessive scar tissue to block the filtering channel or bleb that has been made. Since many of the cells in the tissue abutting the wound site are amitotic (non-dividing); the antimitotic agents would have little or no effect on these cells, thus conferring additional selectivity to the use of the implant.

A sufficient amount of the modulating agent bound to the polymer implant is introduced into the surgical wound site to achieve the desired effect of enhanced healing or inhibition of healing following surgery. An effective concentration is defined as the dose which inhibits cell proliferation using an in vitro assay such as that described above by at least 70%, preferably more than 80%, and most preferably by more than 95% when compared to control plates, i.e., those to which polymer implant alone is added, or as the dose that stimulates cell proliferation by at least 50%, preferably more than 100%, and most preferably by more than 200% when compared to control plates. An effective modulating dose of the modulating agent for inhibiting wound healing in GFS generally is in the range of 10–500 μg, more preferably 10–200 μg, still more preferably 10–100 μg.

In another use of the invention, the tissue(s) and cells of interest are the lens capsule and any associated residual lens epithelial cells following cataract surgery. The invention is used to prevent growth of the residual lens epithelial cells on the lens capsule after removal of a primary cataract. The primary cataract can be of any type, including senile, juvenile and radiation-induced. The polymer implant can inhibit proliferation of, or preferably kill, lens epithelial cells which can grow across the optic axis of the posterior lens capsule following removal of the primary cataract. For evaluation of the efficacy of the invention for use in the prevention of secondary cataract following primary extracapsular cataract surgery, an art accepted in vitro model can be used. Cataract surgery is performed in a host animal such as a rabbit according to methods described by Ulrich, et al., ((1993) *J. Cat. Refract Surg.* 19:462). Following surgery, a polymer implant is inserted into the capsular bag. The implant is crafted in the form of an open loop or ring the diameter of which approximates the lens equatorial diameter. Both ends of the loop are placed inside the bag using techniques common for placement of intraocular lens haptics. Various concentrations of the cell proliferation-modulating agent are absorbed to the implant. Following surgery, eyes are observed to determine the effect of the implant on lens epithelial cells proliferating on the posterior capsule surface. At selected times following surgery, animals are humanely sacrificed and the eyes are submitted for histological evaluation to assess the degree of lens epithelial cell proliferation.

The development of secondary cataract in humans can take from a few months to several years. Clinically, secondary cataract is determined by slit lamp microscopy presenting as the appearance of lens epithelial cells growing on the posterior lens capsule (posterior capsule opacification). This opacification, especially if centrally located, can result in decreased visual acuity. Treatment of posterior capsule opacification is conventionally performed by YAG laser capsulotomy which removes the opacified capsule and restores a clear line of vision resulting in improved visual acuity. The invention described herein, when implanted at the time of primary cataract surgery, allows for the release of therapeutic concentrations of agents cytotoxic for lens epithelial cells. These agents destroy any residual lens epithelial cells and hence prevent their proliferation. Slit lamp microscopy can be used to determine whether posterior capsule opacification has occurred. Alternatively, since posterior capsule opacification can lead to a loss of visual acuity, the maintenance of visual acuity at post-cataract surgery levels or a decreased incidence of YAG capsulotomies can be used to determine the efficacy of the implant.

The subject compositions can be provided as kits for use in one or more operations. Kits can include a separate polymer implant and growth-modulating agent. The agent can be a concentrate, including lyophilized compositions, and can be provided in vials which may include one or more dosages. Conveniently, single dosages can be provided in sterilized containers. Alternatively, the kits can include a composition prepared for direct use. Generally, the growth-modulating agent is combined with the solid support by assembly of the various components in a sterile environment and the assembly is maintained in an aseptic environment until use. The compositions are preferably stored dried or lyophilized in a sterile container. Excipients may be used to promote stability under these conditions. Generally if the drug is currently stable under these conditions, it should be stable under the same conditions when associated with an implant. Preferably, the implant should be kept dry until it is ready for implantation.

The following examples are offered by way of illustration and not by way of limitation.

EXAMPLE 1

Cytotoxic Activity of Ricin Associated with Polystyrene

Ricin (Sigma Chemical Company) was diluted in phosphate buffered saline (PBS) to prepare a dilution series of 20, 2.0, 0.2, 0.02 and 0.002 μg protein/ml. Ricin dilutions were added to duplicate wells (0.5 ml/well) of a 24 well polystyrene culture plate (Corning). PBS was added to two additional wells as controls. Following incubation for 1 hour at 37° C. and overnight at 4° C. the plates were washed three times with PBS to remove all unbound ricin. ME 180 cells (ATCC No. HTB 33) suspended in 1.0 ml M199 (Gibco) containing 10% fetal bovine serum were added to the wells to give $1.0 \times 10^4$ cells/well and incubated at 37° C. for eight days. Following incubation the culture media was aspirated from the wells and cell monolayers stained by the addition of 0.5 ml crystal violet solution (5% in 70% methanol) to each well. Following incubation for five minutes the plates were washed with water to remove excess stain and allowed to air dry. Plates were then inspected with an inverted microscope and the degree of cell growth (percent confluence) was estimated. Results are shown in Table 1, below.

TABLE 1

Cell Proliferation in Polystyrene Culture Wells Pretreated with Ricin

| Pretreatment Concentration (μg/ml)[1] | Percent Cell Confluence[2] |
|---|---|
| 20 | 0 |
| 2.0 | 0 |
| 0.2 | <25 |
| 0.02 | 50–75 |
| 0.002 | 25–50 |
| PBS Control | 50–75 |

[1]Concentration of ricin in PBS added to culture wells.
[2]Percent confluence was estimated by visual inspection of the stained monolayer using an inverted microscope. Zero percent confluence indicates that no cells were observed growing in these wells. One hundred percent confluence would indicate that the well was completely covered with a monolayer of cells.

Thus, this example demonstrates that a modulating agent such as ricin associates with a polymer such as polystyrene and inhibits the growth of cells that contact the coated polymer or are in the vicinity of the polymer implant.

EXAMPLE 2

Release Characteristics of Ricin Associated with Polystyrene Culture Wells

Ricin (Sigma Chemical Company) was diluted in phosphate buffered saline (PBS) to prepare a dilution series of 10, 5.0, 2.5, 1.25 and 0.62, 0.31 and 0.15 μg protein/ml. Ricin dilutions were added to wells (0.5 ml/well) of a 24 well polystyrene culture plate (Corning). PBS was added to additional wells as a control. Following incubation for 1 hour at 37° C. and overnight at 4° C. the plates were washed five times with PBS to remove all unbound ricin. Following washing, 1.0 ml PBS was added to each well and the plate was incubated at 4° C. for 24 hours. Supernatants from individual wells were collected and titrated in a MTT cytotoxicity assay using ME 180 cells. The amount of ricin released into PBS was determined by comparing the cytotoxicity to that obtained with known amounts of ricin. Results are shown in Table 2, below.

TABLE 2

Binding and Release of Ricin from Polystyrene Cell Culture Wells

| Concentration of Ricin Added (μg/ml) | Amount of Ricin Released (ng)[1] |
|---|---|
| 10.0 | 26.2 |
| 5.0 | 12.2 |
| 2.5 | 8.3 |
| 1.25 | 4.6 |
| 0.62 | 4.2 |
| 0.31 | 2.3 |
| 0.15 | 0.84 |

[1]Amount of ricin released from polystyrene following 24 hours incubation in PBS.

Thus, this example demonstrates that the polymer slowly releases the bound modulating agent.

EXAMPLE 3

Binding and Release Characteristics of $^{125}$I-Ricin and Various Polymers

Ricin was labeled with $^{125}$I and diluted to a concentration of 10 μg/ml with a specific activity of $5.8 \times 10^4$ cpm/μg protein. Polymer balls (¼ inch diameter) were purchased from Polysciences and sterilized by autoclaving. Polymer balls were added to the solution of ricin and incubated at 37° C. for one hour and 4° C. overnight. Following incubation unbound ricin was removed by washing the balls with PBS. Individual balls were added to tubes and the amount of associated radioactivity determined by counting in an LKB compugamma counter. Individual balls were also placed in individual wells of a 24 well culture dish containing 1 ml of M199 containing 10% FBS and $4.5\times10^4$ ME 180 cells. Plates were incubated at 37° C. for five days. Following incubation the individual balls were removed from the wells, rinsed and counted for radioactivity. Aliquots of culture media was collected and counted. The remaining media was then pirated and the wells stained and inspected as described above. Results are shown low in Table 3.

TABLE 3

Ricin Associated with Polymer Balls[4]

| Polymer | Pre-Incubation[1] (ng/ball) | Post-Incubation[2] (ng/ball) | Percent Confluence[3] |
|---|---|---|---|
| Polystyrene | 0.677 | 0.397 | 0 |
| Poly-propylene | 1.004 | 0.598 | 0 |
| Acrylic | 0.192 | 0.143 | 0 |
| Polyamide | 0.161 | 0.081 | 0 |

[1]Ricin associated with polymer balls (nanograms/ball) following rinsing and prior to being added to cell culture wells.
[2]Ricin associated with polymer balls (nanograms/ball) after 5 days of culture in wells.
[3]Relative estimation of viable cells attached to cell culture well. Zero indicates no cells.
[4]Controls (balls with no ricin) had percent confluence of 3+.

This example demonstrates that ricin associates with the various polymers and that the ricin which disassociates from the polymer balls during incubation is cytotoxic for cells.

EXAMPLE 4

Cell Proliferation on Daunomycin Associated Nylon Membrane

Nylon membrane discs (Biodyne A, 7.5 mm in diameter, Pall Biosupport) were cut from sheet membrane using a hole punch and autoclaved. The discs were then incubated in a solution of daunomycin (200 μg/ml in PBS) for two hours at room temperature. Discs were visibly red due to the absorbed daunomycin. The discs were rinsed in PBS and placed in M199 and incubated for an additional 2 and ¾ hours. The discs were finally rinsed and blotted to remove excess liquid. The discs were then placed in the bottom of a 24 well culture plate and ten microliters of ME 180 cells suspended in M199 containing 10% FBS was placed in the center of the disc. Plates were incubated at 37° C. for one hour to allow for cell adhesion and then washed to remove unbound cells. M199 containing 10% FBS was added and the plates incubated at 37° C. for 48 hours. To determine the extent of cell proliferation 1 μCi $^3$H-thymidine was added to each well and the plates incubated for an additional 24 hours. The discs were then rinsed in ice cold 10% trichloroacetic acid, rinsed in water and placed in scintillation fluor for counting. Results are presented in Table 4, below.

TABLE 4

Cell Proliferation on Daunomycin Associated Nylon Membranes

| Daunomycin used for Membrane Treatment[1] | Daunomycin in Culture Media[2] | $^3$H-Thymidine Incorporation (cpm[3]) |
|---|---|---|
| − | − | 1627 ± 689 |
| − | + | 62 ± 57 |
| + | − | 29 ± 4 |

[1]Nylon membrane discs were incubated in a solution of daunomycin in PBS and washed to remove unbound daunomycin. Control membranes were treated with PBS.
[2]Following addition of cells control wells received an aliquot of daunomycin in solution sufficient to inhibit cell proliferation.
[3]Incorporation of $^3$H-thymidine into DNA was used to monitor cell proliferation. Data represent the mean and standard deviation of triplicate values.

This example demonstrates that daunomycin associated with a nylon membrane will inhibit cell proliferation as determined by the inhibition of radiolabeled thymidine incorporation.

EXAMPLE 5

Cytotoxic Activity of Daunomycin Associated with Different Polymers

Polymer balls (polystyrene, polypropylene, polyacrylic and polyamide) (¼ inch diameter) were obtained from Polysciences. Individual balls (sterilized by autoclaving) and were placed in a solution of daunomycin diluted to 0.5 mg/ml in PBS and incubated overnight at room temperature. The balls were then rinsed extensively with PBS to remove unbound daunomycin. Individual balls were then placed in wells of a 24 well culture plate (Costar). Additionally a polymethmethylacrylate (PMMA) intraocular lenses (IOL) was treated in a similar manner. A single cell suspension of ME180 cells was prepared by trypsinization of a confluent monolayer and resuspended in M199 containing 10% FBS. One milliliter of cell suspension ($1.4\times10^4$ cells/ml) was added to each well of the culture plate. The plate was incubated at 37° C. until control wells (no balls) reached confluence. At this time the media was aspirated and cell monolayers were stained with crystal violet as described above. The degree of cell growth was determined by visually inspecting the wells for stained cells using an inverted microscope. No cells were observed in any of the wells which contained the daunomycin treated polymer balls or the daunomycin treated IOL. In contrast, wells not containing polymer balls or IOLS had a confluent monolayer of growing cells. This example demonstrates that a polymeric IOL may advantageously be treated with a modulating agent to prevent undesired cell growth on or around the IOL.

EXAMPLE 6

Quantitation of Daunomycin Binding to Different Types of Polymers

Polymer balls (¼ inch diameter) were incubated in a solution of daunomycin as described above. Following incubation and rinsing to remove unbound daunomycin individual balls were placed in one milliliter of methanol to extract bound drug. The absorbance of the methanol extracts was read at 476 nm. Using the extinction coefficient of 173 at 1 cm for a 1% solution of daunomycin and the surface area of the balls the capacity of the polymers was determined. Results are shown below in Table 5, below.

TABLE 5

Capacity of Different Polymers for Binding Daunomycin

| Polymer | Daunomycin bound ($\mu g/cm^2$) |
|---|---|
| Polyamide ball (nylon) | 1.26 |
| Polypropylene ball | 0.50 |
| Polystyrene ball | 0.71 |
| Acrylic ball | 0.28 |

This example demonstrates that a variety of polymers will bind daunomycin, with nylon demonstrating superior binding capabilities.

EXAMPLE 7

Binding and Release Characteristics of Daunomycin with Nylon Membranes

Nylon membrane (Biodyne from Pall) discs, diameter 7.0 mm, were cut from sheet membrane using a punch and autoclaved. The discs were then incubated in a solution of daunomycin (Sigma), 50 $\mu g/ml$ in PBS, for three hours at room temperature. Discs were visibly red in color from the absorbed daunomycin. The discs were thoroughly rinsed with PBS to remove unbound daunomycin. Four discs were added to tubes containing one ml of methanol to extract the bound daunomycin. Daunomycin concentration was determined by measuring the absorbance of the methanol solution at 476 nanometers and an extinction coefficient of 173 for a 1% solution. Eight discs were added to tubes containing one ml of PBS and incubated for 24 hours at room temperature. Following incubation the PBS from tubes containing four of the discs was removed. These discs were extracted with methanol to determine the amount of drug bound to the discs as described above. Incubation of the other four discs was continued for an additional 72 hours (total of 96 hours in PBS). Following incubation the PBS was removed and the discs extracted with methanol to determine the amount of drug bound. Results are shown in Table 6, below.

TABLE 6

Release of Daunomycin from Nylon Membrane Over Time

| | Nylon Associated Daunomycin ($\mu g/disc$) |
|---|---|
| Initial membrane | 16.5 |
| Following 24 hour PBS Extraction | 10.3 |
| Following 96 hour PBS Extraction | 6.5 |

[1]Total daunomycin ($\mu g$) associated per nylon membrane disc. Daunomycin was obtained by extracting from membrane with methanol. Concentration determined by absorbance at 476 nm using 173 (1 cm) as the extinction coefficient for a 1% solution of daunomycin.

This example demonstrates that daunomycin is initially bound to the nylon and is slowly released over time into the surrounding media.

EXAMPLE 8

Nylon-Daunomycin Implant for the Prevention of Secondary Cataracts in a Rabbit Model Secondary cataract typically develops in rabbits within a few weeks following cataract surgery as indicated by proliferation of residual lens epithelial cells on the posterior lens capsule. The effect of a nylon loop-daunomycin implant on the proliferation of lens epithelial cells following cataract surgery is evaluated in vivo in a rabbit model.

Cataract surgery is performed according to methods described by Ulrich, et al., ((1993) *J. Cat. Refract. Surg.* 19:462). Female New Zealand white rabbits are randomly assigned to two treatment groups of six animals per group. Both groups receive lens extraction surgery with phacoemulsification in one eye. The surgical procedure simulates the method used on humans to remove primary cataracts. Animals in group 1 will receive untreated nylon loops. Animals in group 2 receive nylon loops to which one of the test concentrations of the cell proliferation-modulating agents is absorbed. Loops are placed inside the lens capsule following removal of lens material by phacoemulsification.

All of the rabbits receive one week of standard post-surgical care involving anti-inflammatory (topical steroid and antibiotic (topical gentamicin) treatment. Eyes are then observed to determine the effect of the implant on lens epithelial cells proliferating on the posterior capsule surface. At selected times (three and six months), animals are sacrificed and their eyes are submitted for histological evaluation to assess the degree of lens epithelial proliferation.

By implanting the subject intraocular nylon-daunomycin implant into the anterior chamber, remnant lens epithelial cells can be inhibited from proliferating, thus preventing secondary cataracts. The use of an intraocular implant provides a superior means for delivery of cytotoxic drug by allowing for release of drug over time and protection of the drug from degradative processes in the eye. The subject methods and device thus provide a simple procedure for preventing secondary cataracts.

EXAMPLE 9

Nylon-Daunomycin Implant for Control of Scar Formation After Filtering Surgery in Beagles With Glaucoma Beagle dogs are naturally susceptible to glaucoma and are well accepted as a model for human glaucoma. King, et al.

(1991), *Am. J. Vet. Res.* 52:2067–2070. Two groups of six beagles each with glaucoma, as characterized by an IOP of greater than 30 mm Hg in one or both eyes receive glaucoma filtering surgery in one glaucomatous eye; one group receives nylon membrane-daunomycin implant and the other group is treated with nylon filter control. Beagles are given a preoperative eye examination with a Zeiss slit lamp biomicroscope. Preoperative IOP are obtained from the average of three measurements by pneumototometry, using an Applanation Pneumatograph (BioRad), after the installation of one drop of 0.5% proparacaine HCl to each eye. The dog is placed under general anesthesia, a lid speculum placed, a limbal-based conjunctival portame is made approximately 8 mm posterior to the limbus and sharp and blunt dissection performed until the cornea scleral limbus is well visualized. A triangular partial thickness scleral flap is then developed based at the limbus to approximately 50% scleral depth, and then an entry wound into the anterior chamber is made with a sharp 15 degree razor knife. A 1 mm×3 mm sclerostomy is then performed to excise the tissue under the partial thickness flap. A peripheral iridectomy is performed with Vannus scissors and curved jewelers' forceps. The sclera flap is sutured in place with 10-0 nylon suture. A nylon membrane coated with daunomycin is then laid between the sclera and conjunctiva. The conjunctiva is closed with a running absorbable suture.

The animals are then given a combination antibiotic/steroid ointment applied to each eye, are kept warm, and observed every hour for eight hours and then every four hours the following day. Daily observations continue thereafter with the instillation of the antibiotic steroid ointment for approximately 21 days. Examinations including a routine ophthalmic examination for bleb patency, toxicity and complications, slit lamp biomicroscopy and pneumotonometry, are performed daily for the first five days after surgery, then every third day through week six, and then weekly through week twelve. Observations, including variations in IOP, are subjected to standard statistical analysis to look for maintenance of lowered IOP.

EXAMPLE 10

Covalent Coupling of Daunomycin to Polymer Implant Via A Hydrazone Linkage

Nylon membrane discs (Biodyne C, pore size 1.2 micron, 7 mm diameter, Pall Biosupport) having free carboxyl groups were immersed in 30 ml of adipic acid dihydrazide (100 mg/mL in water). One-ethyl-3-3-[dimethylaminopropyl]carbodiimide (EDC) was added to the solution to a final concentration of 3.0 mg/ml and the membrane discs were incubated for 90 minutes at room temperature. The pH was maintained at 4.75 by the dropwise addition of 1.0 M HCl. Following incubation, the membrane was washed extensively with water and added to a solution of daunomycin (3.0 ml, 2.0 mg/ml) in 0.2 M sodium acetate buffer pH 4.5 and incubated for 48 hours at room temperature. Following incubation, the membrane discs were rinsed with PBS to remove unassociated daunomycin. The membrane discs were placed in 100% methanol (1 ml/disc) for 2 hours to remove noncovalently bound daunomycin. A total of 37.2 $\mu$g/disc was removed by this procedure. The discs were placed in a 1:1 solution of methanol and 0.2 M sodium acetate buffer pH 4.5 (1 ml/disc) and incubated at room temperature to extract daunomycin bound to nylon via the hydrazone linkage. After 24 hours, the discs were removed and the extraction buffer saved. The discs were placed in 1 ml of fresh extraction buffer. The amount of daunomycin released into the extraction buffer was determined spectrophometrically. This process was repeated at 48 and 96 hours. In the first 24 hours 37.4 $\mu$g/cm$^2$ was released. At 48 hours an additional 12.15 $\mu$g/cm$^2$ was released. At 96 hours an additional 8.6 $\mu$g/cm$^2$ was released. A total of 58.2 $\mu$g/disc was extracted. Following the above incubations, the discs were slightly red, indicating that some daunomycin was still associated with the nylon. Control membranes that did not receive the hydrazide treatment also bound daunomycin. Substantially all of the daunomycin was removed from these discs during the initial methanol extraction.

EXAMPLE 11

Binding and Release of Daunomycin from Nylon Powder

Nylon 6 pellets (Polysciences Inc., 3 g) were suspended in 100 ml of % 100 methanol containing 20% CaCl$_2$. Following extended incubation (four days) with stirring at room temperature, the nylon solution was added dropwise with stirring into a large excess (2 liters) of water at room temperature. The powder thus obtained was separated on a suction filter and washed successively with water and absolute ethanol and dried under vacuum.

Nylon powder (15.5 mg) was weighed out and ground in a mortar. The powder was added to a 0.5 ml solution of daunomycin (2.2 mg/ml) in PBS and incubated overnight at room temperature. Following incubation, the powder was washed twice with PBS by centrifugation to remove unbound daunomycin. The daunomycin associated powder was resuspended in 1.0 ml of methanol and incubated overnight at room temperature. Following incubation, the methanol was recovered and the powder extracted two more times. The concentration of daunomycin in the extraction solutions was determined spectrophotometrically. The total daunomycin extracted per mg of nylon powder was 51.9 $\mu$g.

EXAMPLE 12

Covalent Coupling of Daunomycin to Carboxymethylcellulose via a Hydrazone Linkage Carboxymethylcellulose (Sigma Chemical Company) low viscosity, 100 mg, was dissolved in water to give a final concentration of 4.0 mg/ml. The pH was adjusted to 4.75 with HCl. Adipic acid dihydrazide (1.75 g) was added to the solution with stirring at room temperature. EDC was added (200 mg) to the solution and the pH was maintained at 4.7 by the dropwise addition of HCL. Following 60 minutes of incubation an additional 200 mg of EDC was added followed by 60 minutes of incubation. The solution was dialyzed against H$_2$O for 72 hours at room temperature followed by dialysis against 0.1 M sodium acetate buffer pH 4.5 for 24 hours. Following dialysis the derivatized CMC was stored at 4° C. The final volume was 30 ml.

Derivatized CMC (CMC-Hz) 5 ml containing approximately 3.3 mg/ml was mixed with 1 mg of daunomycin in 0.1 ml H$_2$O and incubated at 4° C. for 48 hours. The extent of daunomycin association with CMC-Hz was determined by determining the absorbance at 476 nm. One ml aliquots of the CMC-daunomycin complex were precipitated by the addition of 14 ml cold absolute ethanol followed by centrifugation and the precipitate dried. The dried pellet was hydrated by the addition of 1 ml PBS followed by incubation at room temperature. After 3 hours the pellet had swelled and had the appearance and consistency of a gel.

The extent of hydrazide derivatization can be controlled by adjusting the amount of EDC used during the reaction.

Following incubation free daunomycin can be removed by dialysis of the polymer-drug mixture against phosphate buffered saline. The extent of daunomycin association with CMC-Hz is determined by measuring the absorbance at 476 nm.

The release rate of daunomycin from the carboxymethylcellulose as a function of pH can be determined by incubation of individual pellets in aliquots of dilute aqueous (0.1M) buffers at pH 4.5, 5.0 and 7.4 containing 10% acetone. Incubation in each buffer is carried out at 37° C. At each time period the amount of free daunomycin in solution is determined by measuring the absorbance (476 nm) of daunomycin remaining in solution following precipitation of polymer associated daunomycin with absolute ethanol.

EXAMPLE 13

In Vitro Evaluation of Cell Growth Modulating Properties of Implants

Polymer implants coated with agents that modulate cell proliferation can be evaluated in vitro. Cell culture wells are loaded with one ml M199 medium containing 10% FBS. The implant polymer coated with cell proliferative agent is added to the wells. Culture wells are then seeded with cells from the tissue of interest, for example, scieral or conjunctival-derived fibroblasts or lens epithelial cells, and incubated for a sufficient time with the growth-modulating composition to observe the desired effect. Growth is determined for each plate by any method known to those skilled in the art, such as trypan blue dye exclusion, tritiated thymidine incorporation and the like. Cell growth aiso can be determined by direct microscopic visualization of cells, either stained or unstained. Alternatively cell growth can be determined using the vital dye MTT (3-(4,5-dimethylthiazol-2y)-2,5-diphenyl tetrazolium bromide. This dye is converted to a blue formazan product by living cells, but not dead cells (Mosman, *J. Immunol. Methods* (1983) 65:55). The blue product is then solubilized with sodium dodecyl sulfate/HCl and quantitated on an ELISA reader at 590 nm. The $IC_{50}$ value is determined by the concentration of agent that causes killing of 50% of the cells compared to the untreated control wells.

EXAMPLE 14

Evaluation of Implant for Enhancement of Cell Proliferation During Wound Healing The polymer implant with associated cell proliferation modulating agent can be evaluated in any of a number of art accepted wound healing models. Especially relevant in this instance are models which incorporate surgical wounds. The polymer implant, coated with cell proliferation modulating agent, for example, transforming growth factor type beta (TGF type beta), is placed subconjunctivally in rabbit eyes. New Zealand white rabbits are placed under general anesthesia and a lid speculum is placed in the eye. A limbal based conjunctival flap is created by incision of the conjunctiva and blunt dissection forward to the limbus. Care is taken not to cut the episclera. The implant is placed under the flap and the conjunctiva is closed with 9-0 vicryl suture in a running-looking fashion.

Animals are sacrificed on days 3, 5 and 7 following implantation. The eyes are enucleated and fixed in neutral buffered formalin. Paraffin sections of tissue containing the implant are prepared, followed by staining with hematoxylin and eosin to observe the degree of fibrovascular proliferation at the implant site. Staining of sections with Massons trichrome is performed to observe newly formed collagen fibers at the implant site. The degree of fibrovascular proliferation and the amount of newly formed collagen in and around the implant is substantially greater in tissue receiving implants coated with TGF type beta as compared to implants with no agent or tissue not receiving an implant.

EXAMPLE 15

Hyaluronic Acid-Daunomycin Implant for Control of Wound Healing Following Filtration Surgery.

A hyaluronic acid-daunomycin implant was constructed to evaluate implant for control of wound healing following filtration surgery in a rabbit model. Bovine hyaluronic acid (HA) (Sigma Chemical Company), 100 mg, was dissolved in water to give a final concentration of 4.0 mg/mL. The pH was adjusted to 4.75 with HCl. Adipic acid dihydrazide (2.0 g) was added to the solution with stirring at room temperature. EDC was added (50 mg) to the solution and the pH was maintained at 4.7 by the dropwise addition of HCl. Following three hours of incubation at room temperature the solution was dialyzed against H2O for 24 hours at room temperature, followed by dialysis against 0.1 M sodium acetate buffer pH 4.5 for nine hours.

Dervitized HA (HA-Hz) was mixed with 25 mg daunomycin (DM) (Sigma Chemical Company) dissolved in 1.5 mL H2O and incubated 24 hours at 4° C. The slight precipitate which formed was removed by centrifugation. The supernatant was collected and diluted to a final volume of 100 mL with H2O and passed over a 5 micron filter. Six mL aliquots were added to individual 50 mL centrifuge tubes followed by the addition of 0.250 mL HA (4.0 mg/mL). The HA and covalently bound DM was precipitated by adjusting the volume to 35 mL using sterile ethanol followed by centrifugation. The precipitate was washed once with ethanol and transferred to a 15 mL conical centrifuge tue and centrifuged again. Following centrifugation the ethanol was removed by decanting and the pellet dried in a vacuum jar overnight at 4° C. Once dry the pellets were weighed, transferred to vials, capped and stored at 4° C. Individual pellets were rehydrated in 2.0 mL of phosphate buffered saline and the absorbance read at 480 nm. The HA associated daunomycin was determined to be 250 µg DM per 10 mg HA pellet.

New Zealand White rabbits weighing between 1.5 and 2.0 kg were anesthezied by injection of ketamine (33 mg/kg) and xyalizine (6 mg/kg) intramusculary. A lid speculum was used to expose the globe. The conjuctiva was incised supertemporally near the fornix with Wescott scissors. Tenectomy was performed to expose the underlying sclera, followed by careful conjunctival dissection anteriorly to the limbus. A 5 mm limbal grove extending 3 mm into the clear cornea was made with a #57 Beaver blade. A 1 mm by 3 mm scierostomy was made with a Kelly-Descement punch, followed by cautery of the posterior lip. A peripheral iridectomy was then performed. The conjunctiva wound was partially closed with 10-0 nylon sutures in a continous fashion. Prior to complete closure a HA-DM pellet (implant) or HA implant (Placebo) was placed under the conjunctiva just proximal to the scierostomy. Control rabbits underwent surgery but did not receive implants. Following closure, sterile saline was injected to reform the anterior chamber and to ensure the wound was watertight. Finally topical Maxitrol was instilled in the eye.

Both eyes of each rabbit were examined prior to and following surgery. Intraocular pressures were determined using a Digilab pneumotonometer at each examination. The difference in intraocular pressure between the control eye (no surgery) and the eye receiving surgery was determined for each animal. On postoperative days 1 to 3, no significant difference in IOPs were observed between groups. The reduction in IOPs for control, placebo implant and HA-DM implant on day 3 were 11.6+/−1.6, 10.8+/−2.7 and 14+/−0.98 mm of Hg respectively. On days 4 through 7, the control and placebo implant groups showed a gradual return to preoperative IOP levels, and by day seven, no significant differences in IOP's compared to pre-operative values were observed. In Ha-DM implanted rabbits, IOP's on day 7 were reduced from preoperative values by 11.8+/−3.2 mm of Hg. This reduction is IOP was significantly different from both control and placebo HA implant groups. IOP's in the HA-DM implanted group remained at these levels until studies were terminated on day 16. In control and placebo-implanted rabbits, bleb size started decreasing on day 1 and by day 7, no blebs were observed. In the HA-DM implanted rabbits, diffusely elevated microcystic blebs were observed until the end of the experiment on day 16. These studies provide evidence that the controlled release of daunomycin from such implants can significantly improve the success of filtering procedures.

EXAMPLE 16

Reduction Of Adhesion Formation Using A Carboxymethylcellulose-Daunomycin Conjugate Barrier Implant Reduction of adhesion formation is examined in a rabbit uterine horn model using a carboxymethylcellulose-daunomycin (CMC-DM) conjugate barrier implant as described below. Carboxymethylcellulose of viscosity 1,500 to 3,000 cps is derivitized and conjugated to daunomycin as described above in Example 12. Following removal of free daunomycin, 10 mL of a 1.6% aqueous solution of CMC-DM containing 1 mg DM is pipetted into 60 mm tissue culture dishes and allowed to gel at 40 for 1 hour. The dishes are then cooled to −70° C. for at least 1 hour and lypholyzed to form a dry spongelike wafer.

Twenty-five New Zealand White female rabbits of reproductive age, 2.5–4.3 Kg are obtained from local vendor. Before laparotomy, each animal is anesthetized with ketamine hydrochloride 40 mg/kg and xylazine 10 mg/kg body weight given intravenously. The abdomen is shaved and cleaned with povidone-iodine solution and draped with sterile sheets for abdominal surgery. Each animal undergoes laparotomy through a 4–5 cm midline abdominal incision, beginning slightly inferior to the umbilicus. The bowels are carefully packed into the upper abdomen with a moist laparotomy sponge and a pediatric Balfour retractor. The uterine horns are identified and experimental injury is produced in an identical manner to both horns by making transverse cuts in the serosal and muscular layer, 1 cm apart with a clean knife at the antimesentric border. Hemostasis is achieved by use of bipolar diathermy. Thereafter one side is left uncovered and the opposite side covered with either the CMC-DM barrier implant or CMC alone as a control. The abdomen is then closed in three layers with 5-0 Vicryl. The skin would is covered with getamician ointment 0.1%. All animals receive a intraoperative dose of antibiotic, penicillin G, benzathine injection 1.2 MU intramuscularly.

All animals are allowed to recover routinely. Four weeks following surgery, each rabbit is euthanized by injection of 60 mg/kg thiopental intravenously. A second laprotomy is then performed and the pelvic adhesions graded. The scoring system considers the extent and severity of the adhesions along the length of the traumatized area of the horn. The extent of adhesions are measured as follows: 0, no adhesions; 1, adhesions present on 25% of the traumatized area; 2, 50% of traumatized area; 3 total involvement. The severity (tenacity) of the adhesions are measured as follows: 0, no resistance to separation; 0.5, some resistance (moderate force required); 1, sharp dissection needed. The total grade is determined by adding the two scores giving the total range of adhesion scores from 0 to 4, which represents both extent and severity. The extent and severity of adhesions is substantially greater for traumatized uterine horns receiving no treatment as compared to uterine horns receiving the CMC-DM barrier implants. The CMC barrier without daunomycin is intermediate between the two.

EXAMPLE 17

Binding of Daunomycin to Acid Treated Nylon Suture

Nylon suture (polyamide non-absorbable surgical suture, size # 1, S. Jackson, Inc.) was cut into four centimeter sections. Individual sections were placed in tubes containing increasing concentrations of HCl and incubated at 45° C. for one hour and fifteen minutes. Following incubation the sections were thoroughly rinsed with water followed by a single rinse with PBS. The sections were then placed in a solution of daunomycin in PBS and incubated overnight at 4° C. Following incubation the sections were rinsed with water to remove unbound daunomycin. Bound daunomycin was extracted from the sections by incubation in 2.0 mL methanol and absorbance determined at 480 nm. Results are shown below in Table 7. Treatment of nylon with increasing concentrations of HCl resulted in the enhanced binding of daunomycin.

TABLE 7

| HCl Concentration (N) | Suture Associated Daunomycin ($\mu$g/4 cm section) |
|---|---|
| 2.92 | 72.2 |
| 2.19 | 19.3 |
| 1.46 | 5.2 |
| 0.73 | 1.4 |
| 0.0 | 0.89 |

EXAMPLE 18

Covalent Coupling of Mitomycin C to Cyanogen Bromide Activated Carboxymethylcellulose Carboxymethylcellulose (Sigma Chemical Company), 100 mg was dissolved in water to give a final concentration of 5.0 mg/mL. The pH was adjusted to 10.7 with NaOH. Cyanogen bromide (Aldrich), dissolved in acetonitrile to a concentration of 500 mg/mL, was added in six 50 ul aliquots over 5 minutes with continual stirring. The pH was maintained at 10.7 to 11.2 by the dropwise addition of NaOH. After incubation for an additional five minutes the pH was adjusted to 7.5 with HCl and the activated CMC was mixed with 2.0 g of 6-amino-u-hexanoic acid (Sigma) and 2.0 mL of concentrated (10×) PBS followed by incubation at room temperature for two hours. Following incubation the reaction mixture was dialyzed overnight against water. Following dialysis the solution was further dialyzed against 10 mM MES buffer pH 5.6 overnight at room temperature. Ten mL of derivitized CMC was mixed with two mg mitomycin C (MMC) (Sigma) and 52 mg EDC and incubated for one hour at room temperature in the dark. An additional 50.4 mg was then added and incubation continued for another hour. Following incubation MMC associated CMC was dispensed into 15 ml centrifuge tubes at 2.0 mL/tube and precipitated by the addition of 1 mL 1.5 M NaCl in phosphate buffer (pH 7.2) and 12 mL ethanol followed by centrifugation. The supernatant was decanted and the remaining blue precipitates were dried under vacuum. The weight of the dried precipitate in a tube was determined and then hydrated by the addition of 2.2 mL PBS. The amount of CMC associated MMC was determined by measuring the absorbance at 364 nm. The average CMC-DM precipitate weighed 18 mg and contained 248 μg MMC. These data show that the amino group of 6-amino-n-hexanoic acid can react with the cyanogen bromide activated hydroxyl groups of CMC and that the resulting terminal carboxylic acid group can be used for coupling of MMC.

EXAMPLE 19

Covalent Coupling of Daunomycin to Cyanogen Bromide Activated Hydroxypropylmethylcellulose Hydroxypropylmethylcellulose (HPMC) (Sigma Chemical Company), 100 mg was dissolved in water to give a final concentration of 5.0 mg/mL. The pH was adjusted to 10.7 with NaOH. Cyanogen bromide (Aldrich), dissolved in acetonitrile to a concentration of 500 mg/mL, was added in six 50 ul aliquots over 5 minutes with continual stirring. The pH was maintained at 10.7 to 11.2 by the dropwise addition of NaOH. Following incubation for an additional five minutes the pH was adjusted to 7.5 with HCl. Then mL of the activated HPMC solution was mixed with 1.0 g of adipic acid dihydrazide (Sigma) followed by incubation at room temperature for two hours. Following incubation the reaction mixture was dialyzed overnight against water. Following dialysis the solution was dialyzed against 100 mM sodium aceate buffer pH 4.5 overnight at room temperature. Hydrazide derivitized HPMC (HPMC-Hz) was added to 15 mL conical centrifuge tubes at 1.0 mL/tube and 0.1 mL daunomycin (DM) (5 mg/mL) was added. Tubes were incubated at 4° C. overnight. The HPMC-DM conjugate was collected by precipitation following the addition of 1.0 mL 1.5 M NaCl in phosphate buffer (pH 7.2) and 12 mL ethanol. The red precipitate was collected by centrifugation and dried under vacuum. The weight of the dried precipitate in a tube was determined and hydrated by the addition of 2.2 mL PBS. The amount of HPMC associated daunomycin was determined by measuring the absorbance at 480 nm. The average HPMC-DM precipitate weighed 15 mg and contained 36.9 μg DM. The above results demonstrate that the hydrazide group of a dihydrazide reacts with the cyanogen bromide activated hydroxyl groups of HPMC and that the resulting terminal hydrazide group can react with the carbonyl group of daunomycin.

EXAMPLE 20

Covalent Coupling of Doxorubicin to Sodium Periodate Activated Carboxymethylcellulose Carboxymethylcellulose (CMC) (Sigma Chemical Company), 100 mg, was dissolved in water to give a final concentration of 5.0 mg/mL. Five ml of sodium metaperiodate (Sigma) (20 mg/mL in water) was added to the CMC solution and the mixture was incubated for 2 hours in the dark at room temperature. Following incubation the reaction mixture was dialyzed 24 hours against water. The activated CMC was removed from dialysis and added to 1.0 g adipic acid dihydrazide. This solution was incubated overnight at 4° C. Sodium borohydride (2.5 mL of a 5.4 mg/mL solution in water) was added to reduce Schiff bases and the solution incubated for 3 hours at room temperature. The derivitized CMC (CMC-Hz) was then dialyzed against water overnight at room temperature. Following dialysis in water the CMC-Hz was dialyzed for 8 hours against 100 mM sodium acetate buffer pH 4.5. Following dialysis the CMC-Hz solution was distributed into 15 mL centrifuge tubes at 2.0 mL/tube and 50 μl of doxorubicin (DX) (5.0 mg/mL in water) was added to each tube. Tubes were incubated overnight at 4° C. Following incubation DX associated CMC was precipitated by the addition of 1 mL 1.5M NaCl in phosphate buffer pH 7.2 and 12 mL ethanol followed by centrifugation. The supernatant was decanted and the remaining red precipitates were dried under vacuum. The weight of the dried precipitate in a tube was determined and hydrated by the addition of 2.2 mL PBS. The amount of CMC associated DX was determined by measuring the absorbance at 495 nm. The average CMC-DX precipitate weighed 11.7 mg and contained 34.6 μg DX. This example demonstrates that the hydrazide group of a dihydrazide can react with aldehyde groups formed by the limited sodium periodate oxidation of CMC. Reduction of the resulting Schiff bases with sodium borohydride results in a derivatized CMC molecule containing multiple hydrazide groups which can subsequently react with the carbonyl group of doxorubicin.

EXAMPLE 21

Characteristics of Conjugation Parameters And Implant Properties

Parameters for implant formulation were evaluated in vitro and in vivo to determine efficacious polymer dose to modulating agent dose ratios using a hyaluronic acid (HA) and daunomycin (DM) model. Table 8 provides an list of some of the conjugation parameters, reagents and implant properties evaluated using the HA-DM implant system.

TABLE 8

| HA-DM Implant Conjugation Parameters and Implant Properties ||| |
| --- | --- | --- |
| Conjugation Parameters | Implant Properties | Effect on Wound Healing |
| Concentrations of: | Solubility | Interaction with ECM and cells |
| HA, DM, Hz, EDC | Viscosity | Availability and presentation of DM to cells |
| Concentration/Drying Conditions | HA Dose | |
| | DM Dose | Anti-proliferative activity |
| | DM/HA Ratio | |

Binding Of Daunomycin To Hyaluronic Acid

The concentration of EDC on derivatization and subsequent binding of daunomycin to hyaluronic acid was evaluated as follows. Derivatization of HA with adipic acid dihydrazide was performed as described in Example 15 with the following exception. EDC was added to give a final concentration of 10.0, 2.4, 0.8, 0.28, 0.1 and 0.0 mg/ml to achieve various degrees of hydrazide derivatization. Conjugation of hydrazide modified HA with DM and removal of free DM was conducted as in Example 15. Results of conjugation are given in Table 9.

TABLE 9

Conjugation of DM to Bovine HA

| EDC (mg/ml) | MSR[1] | µg DM/mg HA |
|---|---|---|
| 10.0 | 20.0 | 22 |
| 2.40 | 19.8 | 21 |
| 0.80 | 17.2 | 18.2 |
| 0.28 | 6.2 | 6.6 |
| 0.10 | 0.15 | 0.16 |

[1]MSR = Molar substitution ratios for individual conjugates were determined by dividing the moles of DM by the moles of HA based on estimated HA molecular weight of 500,000.

The above results demonstrate that the number of reactive hydrazide groups present on the HA polymer effect the molar substitution ratio of the HA-DM conjugates.

To evaluate the effect of HA source and conjugation parameters on the final properties of the HA-DM implant, conjugations were performed with a range of EDC concentrations with different sources of HA. Conjugation of DM with HA from rooster comb and S. zooepidemicus (Sigma) were performed as described in Example 15 for bovine HA. As observed with bovine HA, the implants were found to bind variable amounts of DM depending on EDC concentration. Surprisingly, two differences were observed when compared to the bovine HA-DM conjugates prepared under identical conditions. Preparations of HA from rooster comb and S. zooepidemicus at the higher EDC concentrations gave a gel upon incubation with DM. This gel was able to be precipitated with ethanol and dried to an implant. Upon addition of PBS, however, the conjugates rehydrated to give an intact "hydrogel" appearance but did not go into solution. In contrast, conjugates prepared using lower amounts of EDC did go into solution. Since adipic acid dihydrazide was used in a 30-fold excess it is unlikely that crosslinking occurred.

Release Characteristics of Daunomycin From Hyaluronic Acid

Acid catalyzed release of free DM from HA-DM was examined as follows. HA-DM conjugates were prepared with bovine HA and interspersed in PBS as described in Example 15. The conjugate was precipitated using absolute ethanol, then pelleted by centrifugation, then dissolved in PBS (pH 7.2), 100 mM MES buffer (pH 5.6) and 100 mM sodium acetate buffer (pH 4.7) and incubated at 37° C. Samples were removed at time zero, one, two and four hours and mixed with ethanol to precipitate HA associated DM and the supernatant containing released DM collected. The amount of DM in the supernatants was determined by measuring its absorbance at 480 nm. Release of DM as a percentage of total DM was measured and showed that linking of HA to DM resulted in acid labile linkage of DM to HA.

Level of Hydrazide Derivatization of Hyaluronic Acid-Daunomycin Implants And Its Effect on Release of Free Daunomycin Hyaluronic acid (HA) (20 mg in 5 mL) is derivatized to contain either high, medium or low levels of pendant hydrazide groups using reaction conditions that incorporate adipic acid dihydrazide (0.4 g) and decreasing amounts of EDC (50, 12, and 4 mg). Hydrazide derivatized HA (HA-Hz) is incubated with a specified amount of daunomycin (2.5 mg) to form conjugates having approximately equal amounts of daunomycin per mg of HA-Hz and different levels of unbound hydrazido groups. Hydrolysis of these HA-DM preparations and release of free DM are performed in a physiological solution of phosphate buffered saline (PBS) at 37° C. The samples are loaded into dialysis tubing and dialyzed against 100 mL of PBS. The extent of hydrazide derivatization (number of pendant hydrazido reactive groups) and its effect on the release of free DM is determined by monitoring change in absorbance of the dialysate at 480 nm.

Drying and Concentration Characteristics Of Implants

HA-DM implants were prepared as described in Example 15 followed by ethanol precipitation and drying in a vacuum to maintain the long term stability of DM. Other methods of concentration and drying, including rotary evaporation and air drying from an aqueous film, are tested to examine rehydration and solubility properties on HA when conjugated to DM. Conjugation of HA and DA is performed as described above and aliquots are: 1) dried under vacuum following ethanol precipitation; 2) cast as an aqueous film and air dried at various temperatures; and 3) lyophilized. Following drying, samples are evaluated for rehydration and solubility is determined by immersing the implant in 2.0 ml PBS under constant agitation and temperature. Extent of solubility is tested, besides visual assessment, by high speed (10,000×g) centrifugation and spectrophotometric analysis for detection of particulates. Implant stability and activity parameters with and without excipients are determined in short term accelerated and/or long term stability experiments following parameters outlined in Table 8.

Binding Affinity of Hyaluronic Acid-Daunomycin Implants To Human Ocular Tissue

Binding of HA by HA-specific binding proteins associated with the extracellular matrix (ECM) and on cell surfaces of human ocular tissue is examined as follows. HA-DM implants prepared as above, dissolved in PBS, and tested for binding properties. The implants are tested for their binding properties to HA binding proteins using biotinylated HA probes prepared according to methods known in the art. The binding affinity of the implants and the effect of the number of pendant terminal hydrazido reactive groups and DM concentration are compared by detection of the biotinylated bound probe by standard means.

Molecular Weight, Viscoelastic and Shear Properties Of Implants

Implant properties contributed by molecular weight and viscosity of HA are evaluated as follows. Different molecular weight HA ($1 \times 10^5$ to $2 \times 10^6$) are obtained from natural or commercially available sources and tested for conjugation. Low molecular weight HA is prepared by subjecting high molecular weight HA to limited enzymatic digestion using hyaluronidases and passed over a Sepacryl S-500 HR column for fractionation. Fractions corresponding to various molecular weight ranges are pooled and concentrated to 4 mg/ml. Molecular weight is estimated from limiting viscosity number in 0.15 M NaCl. Intrinsic viscosity and shear properties is determined with a Cannon Ubbelonde semimicro dilution "type 75" viscometer at 37° C. using ASTM standard procedures. HA content is determined by the carbazole method with gluturonolactone as a standard acid as described by Balesz et al. (1993). Total dry weight is determined by drying samples at 50° C. under vacuum. Conjugation and implant properties of the different HA compounds are determined following parameters as outlined in Table 8.

Dose Characteristics Of Implants Against Fibroblast Proliferation In vitro

HA-DM was prepared with bovine HA as described above and compared to free DM for antiproliferative activity against human and rabbit scleral fibroblasts in vitro. Dilutions of HA-DM or DM were prepared in MEM containing 10% FBS in wells of a 96 well plate. Fibroblasts ($1\times10^3$ in 100 µl of media) were added to wells and the plates incubated for 72 hours at 37° C. Following incubation the plates were rinsed and the relative cell density determined by measuring cellular protein. Absorbance values were determined using an ELISA reader at 570 mm. Both HA-DM and DM were significantly cytotoxic for human fibroblast cells as compared to untreated controls. Results with rabbit fibroblasts were similar.

To examine the cytostatic versus cytotoxic dose effect, serial dilutions of HA-DM (µg/ml) were added to wells of a 24 well culture plate. Human scleral fibroblasts (HSF) ($5\times10^3$) in 100 µl of media were added to each well and the plates incubated overnight at 37° C. Following incubation, media from all wells was removed and fresh media without conjugate added. Plates were incubated for an additional five days until control (untreated) wells had grown to confluence. The incubation media was removed by aspiration followed by rinsing the attached cells with PBS. The cells were detached and counted. Data was compared as percent of cells initially added to wells and presented below in Table 10.

TABLE 10

Activity of HA-DM for Human Scleral Fibroblasts in vitro

| HA-DM µg/ml[1] | % of Initial Cells[2] |
|---|---|
| 0.00 | 340 |
| 0.04 | 32.5 |
| 0.12 | 16.7 |
| 0.37 | 0.0 |

[1]DM concentration measured in µg/ml relative to the HA-DM conjugate
[2]Percent of initial cells = Final number of cells/well ÷ Initial number of cells/well The above results show that cells not exposed to conjugate were able to divide and are present 340 percent of the initial cell number. As little as 0.04 µg/ml HA-DM was significantly cytotoxic for HSF cells. This type of assay, when carried out with lower concentrations of HA-DM, permits determination of both the cytotoxic potential of the conjugate and the cytostatic potential, i.e., the dose which inhibits proliferation.

To further evaluate the cytostatic versus cytotoxic dose effect, cultured human fibroblasts and rabbit scleral fibroblast cultures are initiated from explants and propagated in M199 supplemented with 10% FBS. Cells are grown in M199 supplemented with 10% FBS, in a water humidified atmosphere of 5% $CO_2$ in air at 37° C. For each assay, cells are enzymatically detached from established cultures by removing the culture media, rinsing with calcium- and magnesium-free PBS and adding 0.05% trypsin containing 0.05 mM EDTA. Detached cells are washed with PBS and resuspended in M 199 containing 10% FBS. Cells are counted using a hemocytometer and cell density determined. Twenty-four well cell culture plates are loaded with dilutions of HA-DM in media, seeded with $1\times10^4$ cells and incubated for 48 hours. After 48 hours of incubation, 2.0 µCi of $^3$H-thymidine (Amersham) are added to each well and the incubation continued for an additional 24 hours. Following incubation, cells are gently washed with M199 media, and incorporated radioactivity precipitated with cold TCA. TCA precipitates are washed with cold TCA and solubilized with NaOH. Aliquots of each sample are placed in scintillation fluor and counted on a Beckman LS liquid scintillation counter. Radioactivity for all samples is determined after correction for background counts and counting efficiency. Cell associated radioactivity in wells containing HA-DM are compared to wells containing media alone or equivalent amounts of HA. Particular attention is made to determine those concentrations of HA-DM which inhibit cellular proliferation, i.e. those concentrations that are cytostatic rather than those concentrations which are directly cytotoxic. Cytostatic concentrations may be more desirable since cell cytotoxicity in vivo may induce additional inflammation and hence actually promote cell activity and scar formation at the surgical site.

EXAMPLE 22

Dose Response Evaluation Of Hyaluronic Acid-Daunomycin Implants In A Filtration Surgery Model Dose response studies to evaluate the efficacy and toxicity of a given HA-DM implant are performed with rabbits receiving filtration surgery. HA-DM implants with DM doses ranging from 0.025 mg to 1.0 mg covalently associated with 10 mg HA are prepared as described above. Implants containing approximately 0.025, 0.100, 0.250 and 0.750 mg are obtained and used to determine both a minimum efficacious dose and a maximum tolerated dose. Four groups of six animals each receive doses of HA-DM conjugate intraoperatively. A fifth group of six animals receiving only HA serve as controls. An additional group can be added to either the high or low end of the treatment regiment depending on the efficacy and toxicity results. A detailed description of filtration surgery and the post-surgery examination is described below. Animals receive surgery in one eye and are randomly assigned to a immunoconjugate dose. Eyes are randomly assigned for surgery.

As a control, the effect of mitomycin C on post surgical complications are compared with that of the HA-DM implants. Three groups of six animals each receive doses of 0.2, 0.4 or 0.8 mg/ml concentrations of mitomycin C applied with a surgical sponge for five minutes as described by Khaw et al. (1993). These doses are selected as those which cause various degrees of post surgical complications (Khaw et al., 1993) *Ophthalmology* 100 (3):367–372. A third group of six animals serve as vehicle controls. Animals receive surgery in one eye and are randomly assigned to a mitomycin C dose. Eyes are randomly assigned for surgery. Particular attention is made to the identification and detection of post surgical complications occurring with HA-DM and mitomycin C. Slit lamp examination of the anterior segment and histochemical staining of ocular tissue are performed on control eyes and eyes receiving test materials. The post-surgical evaluation methods are described below. Special toxicity parameters which are addressed include: measurement of aqueous flow, electroretinograms and evaluation of bleb strength.

To evaluate the dose response of different HA-DM implant preparations formulated to have various properties (i.e. high and low solubility, high and low viscosity, high and low DM substitution ratios), HM-DM implants are prepared and examined for dose dependent efficacy and toxicity. Comparison is made against the minimally effective dose determined above for implants containing approximately 0.025, 0.100, 0.250 and 0.750 mg. Preparation(s) which are significantly more active at the same DM dose are examined further. Multiple formulation parameters on the final HA-DM implant properties are examined by fractional factorial design statistics known in the art (Box et al., (1978) Statistic for Experimentors (An Introduction to Design, Data Analysis, and Model Building), Eds. John Wiley & Sons, Inc.). for multiparameter drug development.

Filtration Surgery

Glaucoma filtration surgery includes performing full-thickness filtering surgery in rabbits. Animals are monitored for intraocular pressure and bleb potency following surgery. Previous studies have shown that without treatment, aggressive scarring of the bleb and fistula occurs in the rabbit with virtually all filters failing within 14 days.

Dutch Belted pigmented rabbits weighing between 1.5 and 2 kg undergo pre-operative examinations (see below) utilizing slit-lamp biomicroscopy and IOP determined using pneumotonometry. On the day of the surgery, animals are anesthetized with 33 mg/kg of ketamine and 6 mg/kg rompum im. A lid speculum is used to expose the globe. The conjunctiva is incised superotemporally near the fornix with Wescou scissors. Tenectomy is performed to expose the underlying sclera, followed by careful conjunctival dissection anteriorly to the limbus. A 5 mm limbal grove extending 3 mm into the clear cornea will be made with a #57 Beaver blade. Paracentists is made into the clear peripheral cornea nasally and the anterior chamber entered at the fistula site with a #75 Beaver blade. A 1 mm by 3 mm sclerostomy is made with a Kelly-Descement punch, followed by cautery of the posterior lip. A peripheral iridectomy is performed. The HA-DM implant is positioned adjacent to the sclerostomy site. The conjunctiva is repositioned over the implant material and the wound closed with 10-0 nylon sutures in a continuous fashion. Sterile saline is injected through the paracentisis site to reform the anterior chamber, and after ensuring the wound is watertight, topical Maxitrol is instilled. Additional topical antibiotics or steroids are used for 24 hours postoperatively. For those surgeries involving mitomycin C, drug is administered using a surgical sponge prior to creation of the fistual as described by Khaw et al., (1993).

Post Surgical Evaluation

Postoperative rabbit eyes are examined by an observer masked as to the implant status. Rabbits are examined on days 1, 2, 3, 5 and 7 initially, and then again every third day for a total of 21 days or until filtration failure occurs. Slit-lamp biomicroscopy and IOP measurements are performed during each examination. Slip-lamp examination assess the appearance of the bleb, conjunctiva, cornea, anterior chamber and the lens. Special attention is paid to those post operative complications previously observed with antibody. Close attention is made to those post operative complications previously observed with antiproliferative agents such as mitomycin C and 5 FU. These include corneal haze, encapsulated bleb, hyphema, scleral cellularity, aqueous inflow, changes to the ciliary body and epithelium wound leaks and shallow anterior chamber.

IOP Measurements

HA-DM conjugate and mitomycin C are evaluated for their effects on intraocular pressures (IOP) following filtering surgery. The IOPs of drug or implant treated rabbits are compared to the IOPs of rabbits receiving control HA implants and rabbits undergoing filtering procedures without drug or implant. Intraocular pressures are measured with a calibrated Digilab Modular 1 pneumotonometer (Cambridge, Mass.). Three measurements of ipsilateral and contralateral IOP are made and the average values used as the IOPs at that time point. To minimize any discomfort to the animals, corneas are lightly anesthetized by the application of (10 pl) 0.125% proparacaine. To avoid any complications associated with circadian rhythm, IOP are measured at 9 a.m. each examination day following surgery. Statistical analysis of IOP data compare groups using analysis of variance. A "p" value less than 0.05 are considered significant when comparing groups.

Aqueous Flow Measurements

The flow rates of aqueous humor through the anterior chamber are measured in vivo by various physical measurements known in the art including measurement of decay of radioactive agents and fluorophotometry. Fluorophotometry can be conducted using a Fluorotron Master (Coherent Instruments, Palo Alto, Calif.) to measure the changes in fluorescein concentrations in the cornea and aqueous humor. Anterior chamber and corneal volumes are based on ultrasound measurements of the anterior chamber depth and corneal thickness and calculated by employing the geometric formula of a sperical segment and a cylinder, respectively. The determinations of anterior chamber and corneal fluorescein concentrations and volumes are used to estimate the change in the total mass of fluorescein in the anterior segment with time. The rate of aqueous flow, F, then can be determined from the following equation: $F = \Delta m/\Delta t/c_a$, where $\Delta m$ is the change in the total mass of fluorescein, $\Delta t$ is the time interval between measurements and $c_a$ is the average concentration of fluorescein in the anterior chamber over the time interval.

Electroentinograms

Electroentinograms (ERGs) are used to provide functional assessment of the retina prior to and following HA-DA implantation. ERGs are recorded by means of AgCl electrodes in contact with the cornea and tongue via agar bridges. A reference ground electrode is placed under the scalp. Light stimulation (700 lux) is provided by a Grass PS22 photosimulator in conjunction with a series of neutral density fibers. Signals are amplified by a DAM 50 differential amplifier (World Precision Instruments) and digitized and stored on a computer. For ERG measurements, the corneas for the test eye (i.e. eye receiving implant) and contralateral eye are anesthetized and the iris dilated by topical administration of tetracaine (0.5%) and atropine (1.0%). Single flash (10 psec. duration) white light stimuli is used to elicit ERG and b-waves. Peak a-wave amplitudes are measured from baseline to the trough of the a-wave. Peak b-wave amplitudes are measured from the trough of the a-wave to the peak of the b-wave. The time interval from the onset of the flash to the peak of the a- and b-wave is used for latency measurements.

Bleb Strength

Bleb strength is assessed by determining the bursting pressure of the bleb (i.e. pressure required to produce a leak in the filtering bleb). The dose of DM in the implant or mitomycin C is set equal to the $ED_{50}$ value determined from previous dose response studies. The anterior chamber is calculated with a 21 guage needle and connected to a Harvard infusion pump and pressure transducer. Signals from pressure transducer is amplified and recorded (2 Hz) by a computerized data acquisition system, and displayed and recorded on a computer system. The eye is perfused with Barany's solution (NaCl 8 g/l, KCl 0.35 g/l, CaCl 0.17 g/l, $MgCl_2$ 64 mg/l, $Na_2\ PO_4$ 69 mg/l, NaH2 PO4 13.7 mg/l, glucose 1 g/l) at a rate of 50 Hg/minute producing a rise in IOP of 20 to 25 mm of Hg/minute. The bursting pressure is defined as the peak pressure reached during the perfusion that is followed by a rapid reduction in pressure at the time the bleb perforates. Fluorescien staining is used to confirm the site of the perforation. A minimum of four determinations are conducted to determine the average bursting pressure.

Histochemical Analysis

At the termination of the study or at the time of filtration surgery failure, animals are sacrificed by an overdose of sodium pentobarbital and the eyes removed for histologic and immunochemical examination. The criteria for failure of the filtering procedure is the return of IOP to within 2 mm of Hg of the original IOP for three consecutive days. Histochemical analyses of eye tissue sections obtained from rabbits receiving HA-DM implants are performed to determine localization of DM and residual HA-DM. Enucleated eyes are fixed in 1% glutaraldehyde and 10% formalin for 24 hours and tissues dehydrated in ethanol and embedded in paraffin. Sections are stained with hematoxylin and eosin and photographed on a Zeiss photomicroscope. Selected tissues are stained with anti-DM antibody to test for residual HA-DM conjugate following procedures known in the art. For these experiments, antiserum specific to daunomycin conjugated to hydrazide derivitized bovine serum albumin (BSA-Hz-DM) is prepared using procedures outlined for hydrazide-based conjugation of HA and DM. (*J. of Glaucoma* 1:87). Antibodies against BSA-Hz-DM are prepared following methods known to the art.

Statistical Analysis Of Data

Statistical analysis of data is performed as described by Liang and Epstein (1992) (*J. of Glaucoma* 1:87). Variables analyzed include length of time of IOP control and length of time of bleb survival. IOP control is defined as the presence of a difference between the operated and the unoperated eye. Statistical analysis of IOP is performed using as an outcome the difference between the operated eye of each rabbit and its fellow control eye. Hence, the time to return to normal (control eye) pressure is compared between the various treatment groups. This outcome variable is analyzed by multiple regression to compare groups. The time variables are analyzed using Kaplan-Meier curves and extension of the Wilcoxon and Kruskai-Wallis tests. Means are expressed as +/− standard error.

EXAMPLE 23

Pharmacokinetics Of Hyaluronic Acid-Daunomycin Implants

HA-DM implants are prepared using $^3$H-daunomycin (New England Nuclear) and a pharmacokinetic evaluation is conducted by standard methods known in the art (e.g., Crosson, et al. (1992) (*Exp. Eye Res.,* 55:87–91). Formulation of the HM-DM implant is performed using procedures described above for the optimal dose formulation with the exception that radiolabeled drug is added to derivitized HA prior to unlabeled drug. This stepwise conjugation ensures a maximal specific radioactivity with an optimal dose of DM. Implants are formulated to contain approximately 25 $\mu$Ci $^3$H-DM each. For analysis, representative implants are admixed in 2.0 ml PBS and aliquots added to scintillation fluid and counted in a Beckman LS scintillation counter. Standard tests for HA and DM also are performed on representative implants. The dry weight of each implant is measured to ensure accurate determination of radioactivity in each implant.

Pharmacokinetic studies are conducted using the rabbit filtration surgery model described in Example 22. Eight groups of five animals/group each receive radioactive HA-DM implant as a subconjunctival implant following surgery in one eye. At time zero (15–30 minutes following surgery), at 60 minutes and at 3, 6, 12, and 24 hours, and three and seven days the animal is anesthetized and samples of aqueous humor from the temporal vein collected. The animals are then euthanized by iv. administration of 0.5 ml T-61 (embutramide (200 mg/ml), mebezonium iodide (50 mg/ml), tetracaine hydrochloride (5 mg/ml), the eyes enucleated, and the cornea, iris/ciliary body, lens and posterior sclera/retina dissected free. Urine samples and biopsy samples of liver, kidney, brain and heart also are obtained. Samples are analyzed for $^3$H-DM content using a Beckman scintillator counter. All samples are placed in pre-weighed tubes and sample wet weights determined. Data is expressed as $\mu$g DM/g of tissue and ng DM/ml for blood and aqueous humor samples. Ocular and systemic distribution and clearance of $^3$H-DM are calculated.

The above examples demonstrate that growth modulating agents such as ricin, mitomycin C, doxorubicin and daunomycin can form reversible associations with polymers such as polystyrene, polypropylene, acrylic, polyamide, nylon, hyaluronic acid, carboxymethylcellulose and hydroxypropylmethylcellulose. The modulating agent is then released by the polymer. The association and release can be readily determined using the above experimental methods. The polymer can be crafted into an implant form suitable for the desired application and implanted into an animal. The method can be applied for example to prevent secondary cataracts, to maintain potency of a filtering bleb in GFS or to reduce pelvic and abdominal tissue adhesion formation.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. An implant comprising:
   at least one agent which modulates proliferation of target cells, wherein said agent is bound to a polymer via a reactive group which mediates an interaction selected from the group consisting of: a hydrophobic interaction, a hydrophilic interaction, and a covalent interaction, wherein said interaction is labile under physiological conditions, so that said agent is released from said polymer when contacted with a tissue comprising said target cells without the use of an exogenously supplied releasing agent which changes the physiological conditions in said tissue.

2. The implant according to claim 1, wherein the rate at which said agent is released is controlled so as to restrict said agent to a localized region of said tissue.

3. The implant according to claim 1, wherein said rate is controlled by the molar substitution ratio of said agent to the number of said reactive groups on said polymer.

4. The implant of claim 1, wherein said reactive group is selected from the group consisting of carboxyl, amino, hydroxyl, and hydrazido.

5. The implant of claim 1, wherein said polymer comprises a polysaccharide.

6. The implant of claim 5, wherein said polysaccharide is hyaluronan or a salt of hyaluronan.

7. The implant of claim 1, wherein said polymer is selected from the group consisting of carboxymethylcellulose, polymethylmethacrylate, hydroxypropylmethylcellulose, hyaluronan, nylon, and silicone.

8. The implant of claim 1, wherein said agent inhibits target cell proliferation.

9. The implant of claim 8, wherein said agent comprises an antimitotic.

10. The implant of claim 9, wherein said antimitotic is selected from the group consisting of anthracycline, daunomycin, mitomycin C, and doxorubicin.

11. The implant of claim 8, wherein said agent comprises an antimetabolite.

12. The implant of claim 11, wherein said antimetabolite is 5-flourouracil.

13. The implant of claim 8, wherein said agent is a toxin.

14. The implant of claim 13, wherein said toxin is ricin.

15. The implant of claim 1, wherein said target cells are fibroblast cells.

16. The implant of claim 1, wherein said target cells are epithelial cells.

17. The implant of claim 1, wherein said agent and polymer are bound by a covalent bond.

18. The implant of claim 2, wherein said localized region is a filtration site.

19. The implant of claim 1, wherein said localized region is a lens capsule equatorial region.

20. The implant of claim 1, wherein said localized region is an abdominal surgery site or a pelvic surgery site.

21. An ocular implant comprising: at least one agent which modulates proliferation of target cells bound wherein said agent is bound to a polymer via a reactive group which mediates an interaction selected from the group consisting of: a hydrophobic interaction, a hydrophilic interaction, and a covalent interaction, wherein said interaction is labile under physiological conditions, so that said agent is released from said polymer when contacted with a tissue comprising said target cells without the use of an exogenously supplied releasing agent which changes the physiological conditions in said tissue, and wherein said agent is selected from the group consisting of daunomycin, mitomycin C, doxorubicin, and wherein said polymer is selected form the group consisting of hyaluronic acid, polymethylmethacrylate, hydroxypropylmethylcellulose, carboxymethylcellulose, silicone and nylon.

22. The ocular implant of claim 21 which is a membrane.

23. The ocular implant of claim 21, wherein said implant is selected from the group consisting of an intraocular lens, a drainage shunt, a prosthesis, and a lens capsular loop.

24. The ocular implant according to claim 21 in a form suitable for injection.

25. A method for modulating proliferation of target cells in a localized region of the eye, said method comprising:

contacting a localized region of the eye with an ocular implant according to claim 17.

26. The method of claim 25, wherein said localized region of the eye is a filtration site.

27. The method of claim 25, wherein said target cells are lens epithelial cells.

28. The method of claim 25, wherein said contacting is with an implant or through injection at a surgery site.

29. The method of claim 25, wherein said contacting is at the time of ocular surgery.

30. The method of claim 25, wherein said ocular surgery is cataract surgery or glaucoma filtering surgery.

31. A method of controlling formation of tissue adhesion sites, said method comprising:

contacting tissue at a surgery site with an implant according to claim 1.

32. A method of making a polymer implant comprising at least one agent which modulates proliferation of target cells bound wherein said agent is bound to a polymer via a reactive group which mediates an interaction selected from the group consisting of: a hydrophobic interaction, a hydrophilic interaction, and a covalent interaction, wherein said interaction is labile under physiological conditions, said method comprising: contacting a polymer having a sufficient number of reactive groups with a sufficient amount of an agent which modulates proliferation of target cells to form a bond which is labile under physiological conditions, so that said agent is released from said polymer when contacted with a tissue comprising said target cells without the use of an exogenously supplied releasing agent which changes the physiological conditions in said tissue.

33. The implant of claim 17, wherein said covalent bond comprises a hydrazone linkage.

* * * * *